(12) United States Patent
Adler et al.

(10) Patent No.: US 8,455,289 B1
(45) Date of Patent: Jun. 4, 2013

(54) LOW FREQUENCY CMUT WITH THICK OXIDE

(75) Inventors: Steven Adler, Saratoga, CA (US); Peter Johnson, Sunnyvale, CA (US); Ira Oaktree Wygant, Palo Alto, CA (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 13/309,853

(22) Filed: Dec. 2, 2011

(51) Int. Cl.
*H01L 21/00* (2006.01)

(52) U.S. Cl.
USPC .................................................... 438/53

(58) Field of Classification Search
CPC .... G01L 9/0042; G01L 9/0073; G01P 15/0802
USPC ...... 257/415, 416, 595, E27.016; 310/12.03, 310/311; 600/300, 404, 437; 438/48, 50, 438/51, 53
See application file for complete search history.

(56) References Cited

U.S. PATENT DOCUMENTS

| | | | |
|---|---|---|---|
| 4,837,176 A * | 6/1989 | Zdebel et al. | 438/552 |
| 5,706,565 A * | 1/1998 | Sparks et al. | 29/25.42 |
| 5,894,452 A * | 4/1999 | Ladabaum et al. | 367/163 |
| 2004/0058080 A1* | 3/2004 | Kawasaki | 427/402 |
| 2004/0085858 A1* | 5/2004 | Khuri-Yakub et al. | 367/181 |

* cited by examiner

*Primary Examiner* — Nikolay Yushin
(74) *Attorney, Agent, or Firm* — Eugene C. Conser; Wade J. Brady, III; Frederick J. Telecky, Jr.

(57) ABSTRACT

A capacitive micromachined ultrasonic transducer (CMUT), which has a conductive structure that can vibrate over a cavity, utilizes a thick oxide layer to substantially increase the volume of the cavity which, in turn, allows the CMUT to receive and transmit low frequency ultrasonic waves. In addition, the CMUT can include a back side bond pad structure that eliminates the need for and cost of one patterned photoresist layer.

10 Claims, 23 Drawing Sheets

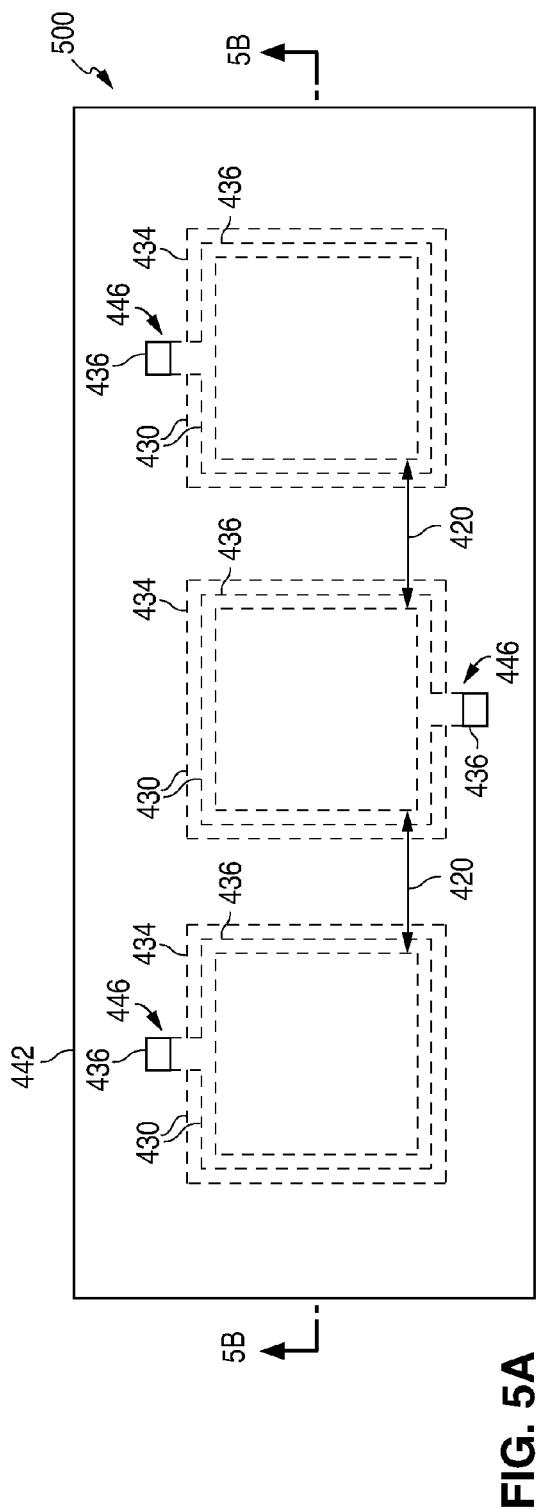
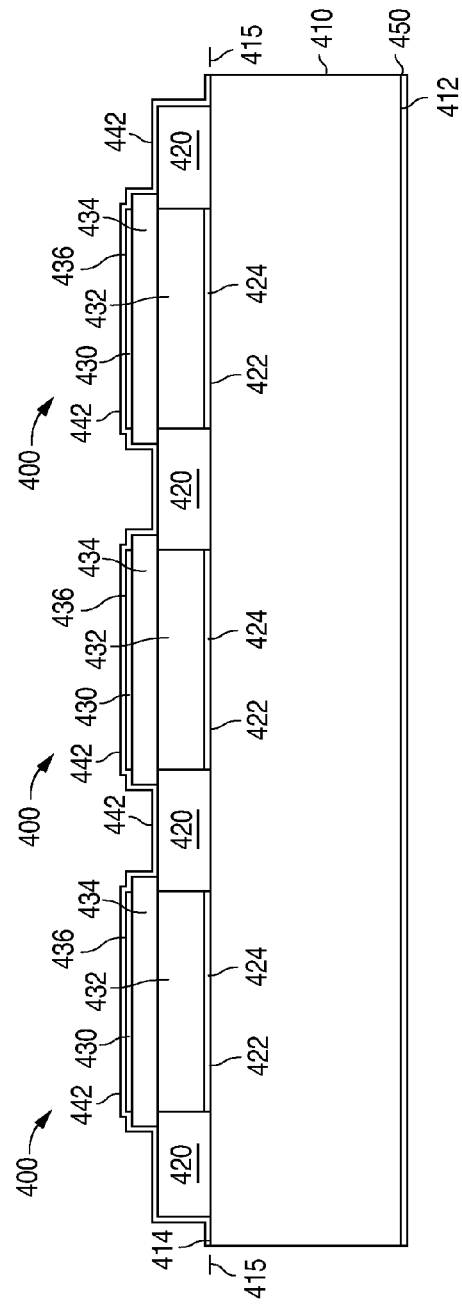
FIG. 5A
FIG. 5B

LOW FREQUENCY CMUT WITH THICK OXIDE

BACKGROUND OF THE INVENTION

1. Field of the Invention

The present invention relates to CMUTS and, more particularly, to a low frequency CMUT with thick oxide.

2. Description of the Related Art

A capacitive micromachined ultrasonic transducer (CMUT) is a semiconductor-based ultrasonic transducer that utilizes a change in capacitance to convert received ultrasonic waves into an electrical signal, and to convert an alternating electrical signal into transmitted ultrasonic waves.

FIGS. 1A-1B show views that illustrate an example of a prior-art CMUT 100. FIG. 1A shows a plan view of CMUT 100, while FIG. 1B shows a cross-sectional view taken along line 1B-1B of FIG. 1A. As shown in FIGS. 1A-1B, CMUT 100 includes a conventionally-formed semiconductor substrate 110, and a post oxide structure 112 that touches the top surface of semiconductor substrate 110. Post oxide structure 112, in turn, has substrate contact openings 114 that extend completely through post oxide structure 112 to expose semiconductor substrate 110.

As further shown in FIGS. 1A-1B, CMUT 100 includes a non-conductive structure 116 that touches the top surface of semiconductor substrate 110, and a conductive structure 120 that touches the top surface of post oxide structure 112 and lies over non-conductive structure 116 to form a vacuum-sealed cavity 122. In the present example, conductive structure 120 includes a semiconductor structure 124 such as, for example, single crystal silicon, and an overlying metal structure 126, such as an aluminum copper plate.

In addition, CMUT 100 includes substrate bond pads 130 that lie within the substrate contact openings 114 to make electrical connections to semiconductor substrate 110, and a passivation layer 132 that touches and lies over post oxide structure 112, conductive structure 120, and the substrate bond pads 130. Passivation layer 132 has substrate bond pad openings 134 that expose the substrate bond pads 130, and a conductor opening 136 that exposes a region of conductive structure 120 which functions as a bond pad. Further, CMUT 100 has an acoustic dampening structure 140 that touches the bottom surface of semiconductor substrate 110.

In operation, a first bias voltage V1 is placed on semiconductor substrate 110, which functions as a first capacitor plate, and a second bias voltage V2 is placed on conductive structure 120, which functions as second capacitor plate. Thus, the voltage across the capacitor plates lies across vacuum-sealed cavity 122. When used as a receiver, an ultrasonic wave causes conductive structure 120 to vibrate. The vibration varies the capacitance across the first and second capacitor plates, thereby generating an electrical signal that varies as the capacitance varies.

When used as a transmitter, an alternating electrical signal applied across the biased first and second capacitor plates causes conductive structure 120 to vibrate which, in turn, transmits ultrasonic waves. The rate or frequency at which conductive structure 120 vibrates depends on the volume of vacuum-sealed cavity 122, and the stiffness of conductive structure 120.

In addition to transmitting ultrasonic waves outward, ultrasonic waves are also transmitted backward towards the bottom surface of semiconductor substrate 110. These backward ultrasonic waves can resonate within semiconductor substrate 110 depending on the thickness of semiconductor substrate 110 and the frequency of operation, and can interfere with the quality of the resultant image. Acoustic dampening structure 140 absorbs and dampens the ultrasonic waves in semiconductor substrate 110.

FIGS. 2A-2B show views that illustrate an example of a prior-art CMUT array 200. FIG. 2A shows a plan view of array 200, while FIG. 2B shows a cross-sectional view taken along line 2B-2B of FIG. 2A. As shown in the FIGS. 2A-2B example, CMUT array 200 includes three CMUTS 100 in a single row.

FIGS. 3A-3N show cross-sectional views that illustrate an example of a prior-art method of forming a CMUT. As shown in FIG. 3A, the method utilizes a conventionally-formed single-crystal silicon wafer 310. Silicon wafer 310 has rows and columns of die-sized regions, and one or more CMUTS can be simultaneously formed in each die-sized region. For simplicity, FIGS. 3A-3N illustrate the formation of a single CMUT.

As further shown in FIG. 3A, the method begins by forming a post oxide structure 312 on the top surface of silicon wafer 310 using the well-known local oxidation of silicon (LOCOS) process. The LOCOS process also forms a backside oxide structure 314 that touches the bottom surface of silicon wafer 310 at the same time. Following this, as shown in FIG. 3B, a cell oxide layer 316 is grown on the exposed regions of the top surface of silicon wafer 310.

After cell oxide layer 316 has been formed, as shown in FIG. 3C, a silicon-on-oxide (SOI) wafer 320 is fusion bonded to the top surface of post oxide structure 312 to form a cavity 322. SOI wafer 320 has a handle wafer 324, an insulation layer 326 that touches handle wafer 324, and a single-crystal silicon substrate structure 328. Substrate structure 328, in turn, has a first surface that touches insulation layer 326, and a second surface that touches post oxide structure 312.

Cavity 322, in turn, has a depth that is measured vertically from the top surface of cell oxide layer 316 to the second surface of substrate structure 328. The thickness of cell oxide layer 316 defines the position of the top surface of cell oxide layer 316. In addition, the height of post oxide structure 312 over the top surface of silicon wafer 310 defines the position of the second surface of substrate structure 328.

The thickness of cell oxide layer 316 is relatively small compared to the height of post oxide structure 312 over the top surface of silicon wafer 310. As a result, the depth of cavity 322 is substantially defined by the height of post oxide structure 312 over the top surface of silicon wafer 310. In addition, substrate structure 328 of SOI wafer 320 is fusion bonded to the top surface of post oxide structure 312 of silicon wafer 310 in a vacuum to vacuum seal cavity 322.

After substrate structure 328 has been fusion bonded to post oxide structure 312, as shown in FIG. 3D, handle wafer 324 is removed in a conventional manner, followed by the conventional removal of insulation layer 326. Next, as shown in FIG. 3E, a patterned photoresist layer 330 is formed on the first surface of substrate structure 328. Once patterned photoresist layer 330 has been formed, as shown in FIG. 3F, the exposed region of substrate structure 328 is etched to form a CMUT membrane 332. Patterned photoresist layer 330 is then removed in a conventional manner.

As shown in FIG. 3G, after the removal of photoresist layer 330, a patterned photoresist layer 340 is formed on post oxide structure 312 and CMUT membrane 332. Once patterned photoresist layer 340 has been formed, as shown in FIG. 3H, the exposed regions of post oxide structure 312 are etched until silicon wafer 310 has been exposed. Patterned photoresist layer 340 is then removed in a conventional manner.

Following the removal of photoresist layer 340, as shown in FIG. 3I, a metal layer 342, such as a layer of aluminum copper, is deposited to touch silicon wafer 310, post oxide structure 312, and CMUT membrane 332. After this, a patterned photoresist layer 350 is formed on metal layer 342.

Next, as shown in FIG. 3J, the exposed region of metal layer 342 is etched to form semiconductor bond pads 352 that extend through post oxide structure 312 to touch silicon wafer 310, and a metal plate 354 that touches the top surface of CMUT membrane 332. Patterned photoresist layer 350 is then removed in a conventional manner.

As shown in FIG. 3K, after patterned photoresist layer 350 has been removed, a passivation layer 356 is formed to touch post oxide structure 312, CMUT membrane 332, the bond pads 352, and metal plate 354. Once passivation layer 356 has been formed, a patterned photoresist layer 360 is formed on passivation layer 356.

After this, as shown in FIG. 3L, the exposed regions of passivation layer 356 are etched to form openings that expose the semiconductor bond pads 352, and an opening, like opening 136 in FIG. 1A, that exposes a bond pad region of metal plate 354. As shown in FIG. 3M, patterned photoresist layer 360 is then removed in a conventional manner.

Next, the resulting structure is flipped over for processing, and backside oxide structure 314 is removed in a conventional manner. For example, backside oxide structure 314 can be removed using chemical mechanical polishing. Alternately, backside oxide structure 314 can be removed using a single-sided wet etch, such as a SEZ etch.

Following the removal of backside oxide structure 314, an acoustic damping structure 362, such as a tungsten epoxy mixture, is deposited onto the bottom side of silicon wafer 310 to form, as shown in FIG. 3N, a CMUT 364. Silicon wafer 310 is then diced to form a number of individual die that each has one or more CMUTS 364.

In the present example, cavity 322 has a depth of approximately 0.2 µm and a diameter of approximately 36.0 µm. In addition, CMUT membrane 332, metal plate 354, and the overlying region of passivation layer 356 vibrate at frequencies of approximately 10-20 MHz. These frequencies are suitable for contact or near contact body imaging applications, like echo cardiograms, but are not suitable for airborne ultrasound applications where, for example, the object to be detected, such as the hand motions of a person playing a game, is one or more meters away.

Instead, airborne ultrasound applications require much lower frequencies, such as 100-200 KHz. If CMUT 364 were scaled up in size to operate at these lower frequencies, then CMUT 364 would require a larger cell diameter (e.g. increasing from about 36 µm to about 1 mm-2 mm), a thicker CMUT membrane 332 (e.g. increasing from 2 µm to 5 µm-40 µm), and a deeper cell cavity 322 (e.g. increasing from 0.2 µm to fpm-12 µm). A deeper cell cavity is required to accommodate the atmospheric deflection of CMUT membrane 332, which can be on the order of several microns. For proper CMUT operation, CMUT membrane 332 should not touch the bottom surface of cavity 322, but rather be a fixed distance of one or more microns above the bottom surface of cavity 322.

Since the height of post oxide structure 312 substantially determines the depth of cavity 322, scaling up CMUT 364 requires that post oxide structure 312 have a height above the top surface of silicon wafer 310 of approximately fpm-12 µm, or a total thickness of 2 µm-24 µm. However, forming a post oxide structure with a thickness that exceeds approximately 5 µm (or heights that exceed 2.5 µm) is difficult to accomplish because the rate of oxide growth slows dramatically when the thickness of the post oxide structure approaches 5 µm.

As a result, it is difficult to scale up CMUT 364 to accommodate these lower frequencies. Thus, there is a need for an approach to forming low frequency CMUTS for airborne ultrasonic applications.

BRIEF DESCRIPTION OF THE DRAWINGS

FIG. 1A is a plan view of CMUT 100. FIG. 1B is a cross-sectional view taken along line 1B-1B of FIG. 1A.

FIG. 2A is a plan view of array 200. FIG. 2B is a cross-sectional view taken along line 2B-2B of FIG. 2A.

FIG. 4A is a plan view of CMUT 400. FIG. 4B is a cross-sectional view taken along line 4B-4B of FIG. 4A.

FIGS. 5A-5B are views illustrating an example of a CMUT array 500 in accordance with the present invention. FIG. 5A is a plan view of array 500. FIG. 5B is a cross-sectional view taken along line 5B-5B of FIG. 5A.

FIG. 7A is a plan view of CMUT 700. FIG. 7B is a cross-sectional view taken along line 7B-7B of FIG. 7A.

DETAILED DESCRIPTION OF THE INVENTION

Figure 1A:
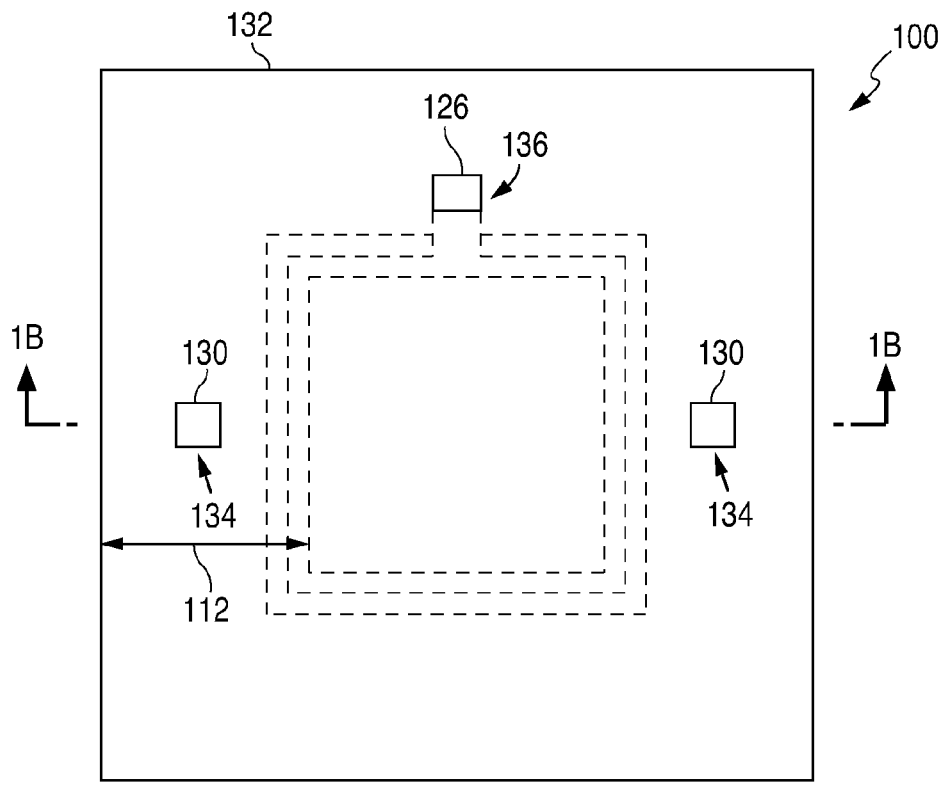
FIGS. 1A-1B are views illustrating an example of a prior-art CMUT 100.
Figure 1B:
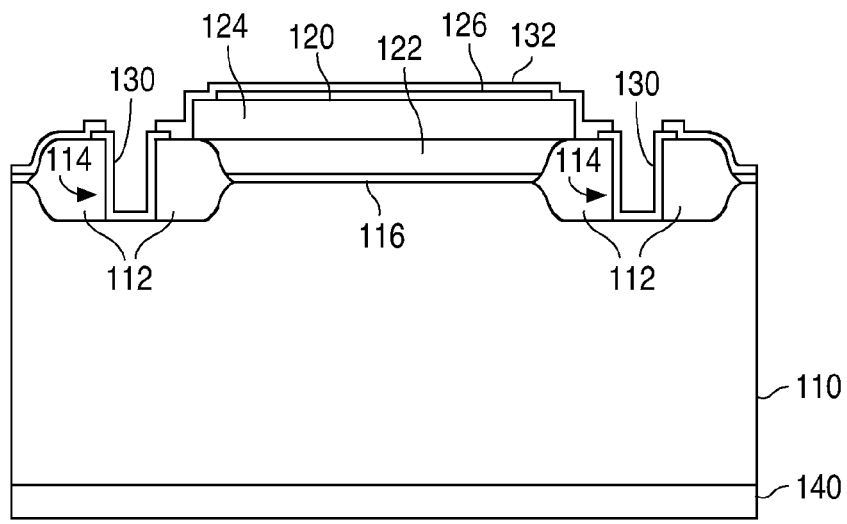
Figure 2A:
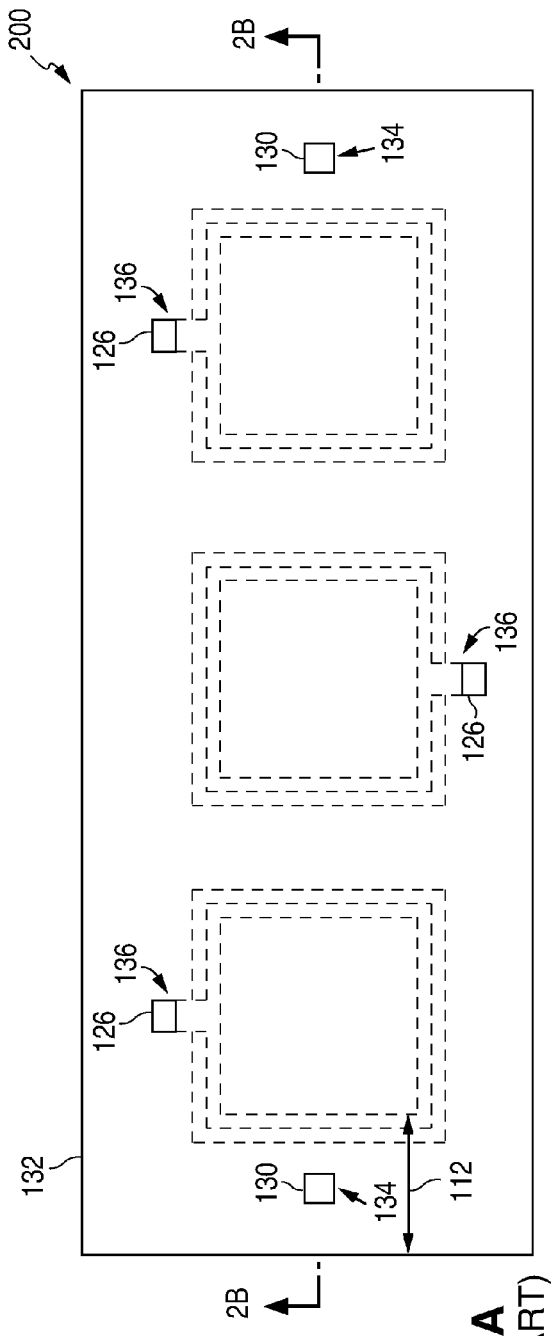
FIGS. 2A-2B are views illustrating an example of a prior-art CMUT array 200.
Figure 2B:
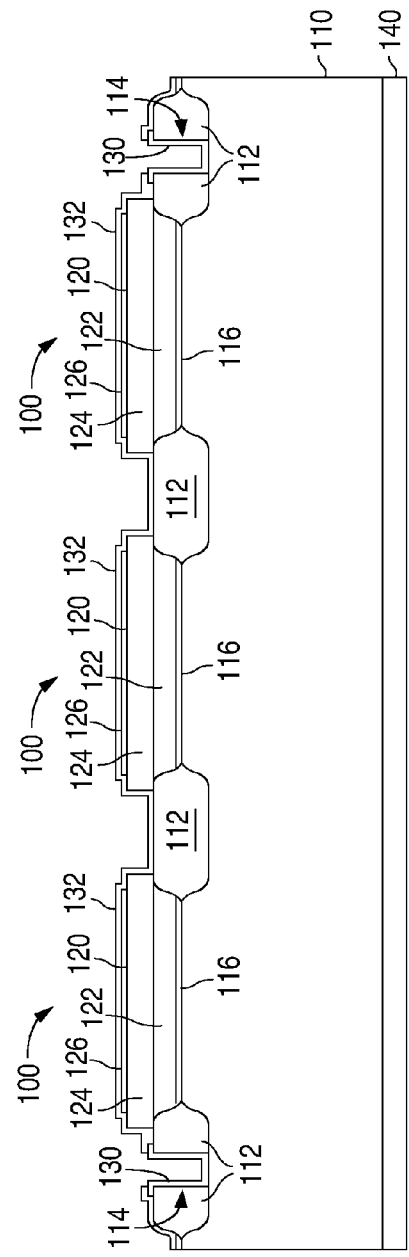
Figure 3A:
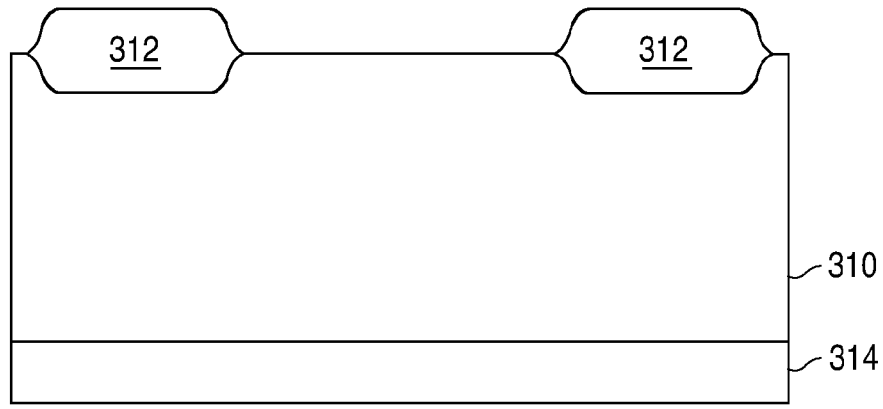
FIGS. 3A-3N are cross-sectional views illustrating an example of a prior-art method of forming a CMUT.
Figure 3B:
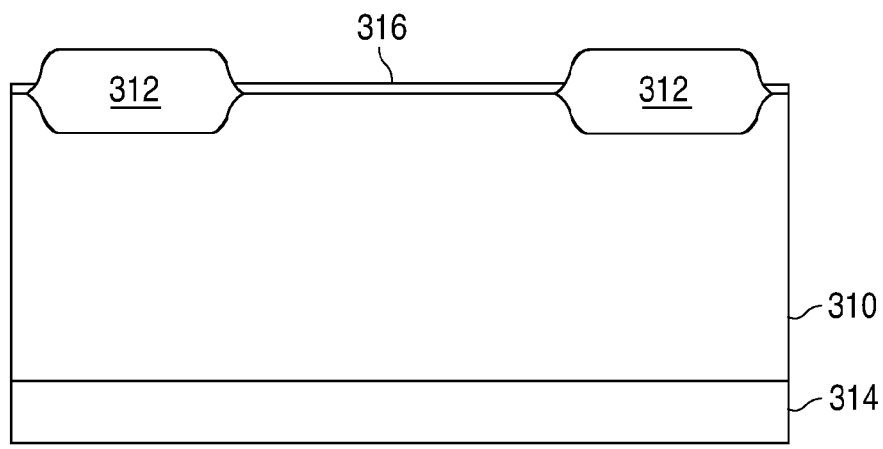
Figure 3C:
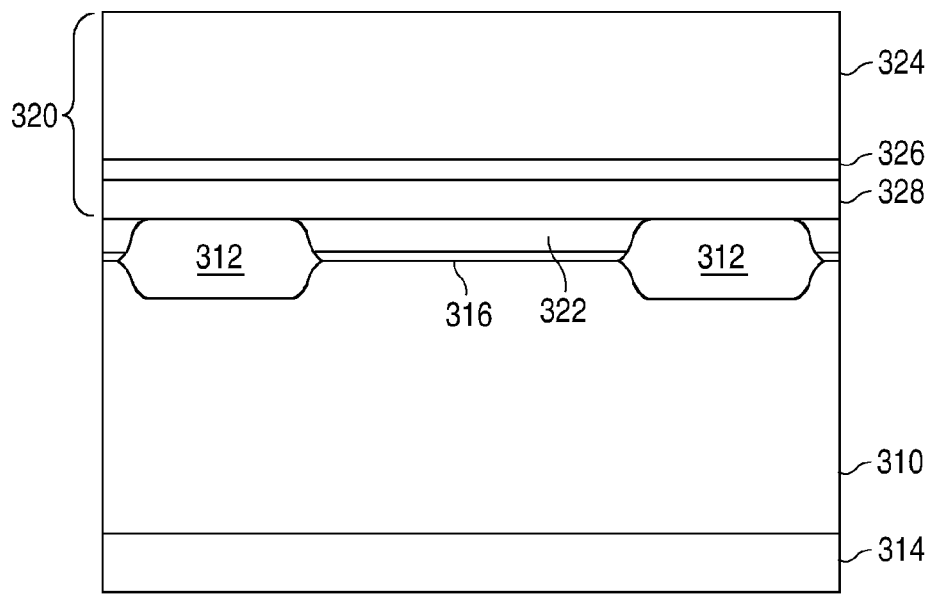
Figure 3D:
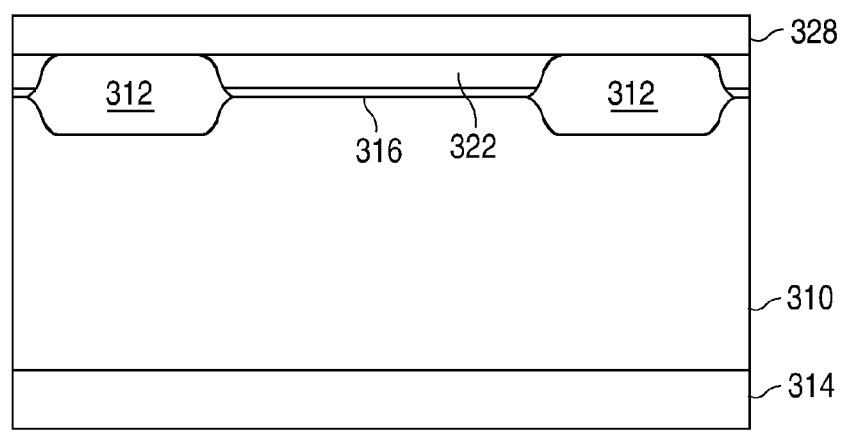
Figure 3E:
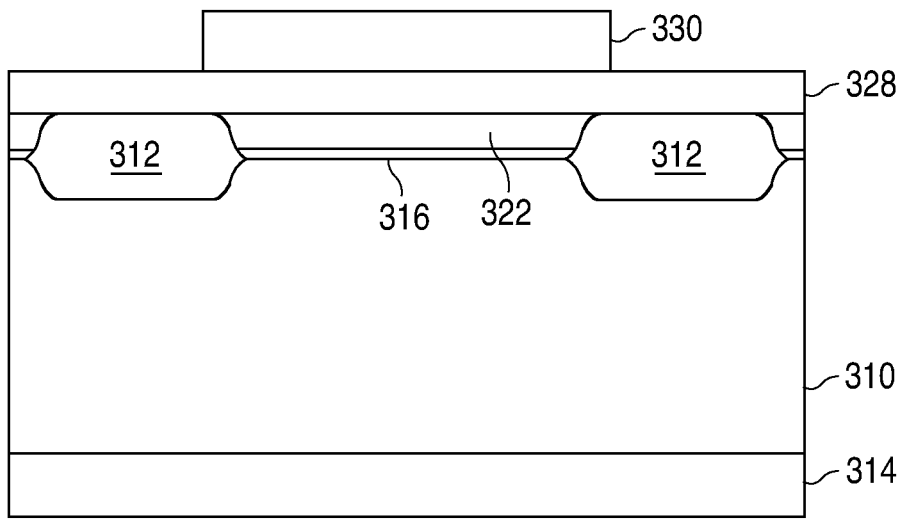
Figure 3F:
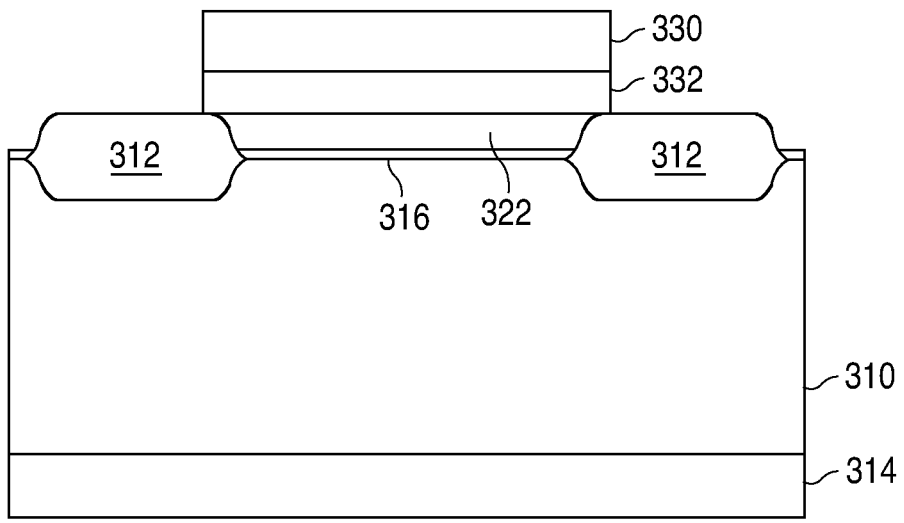
Figure 3G:
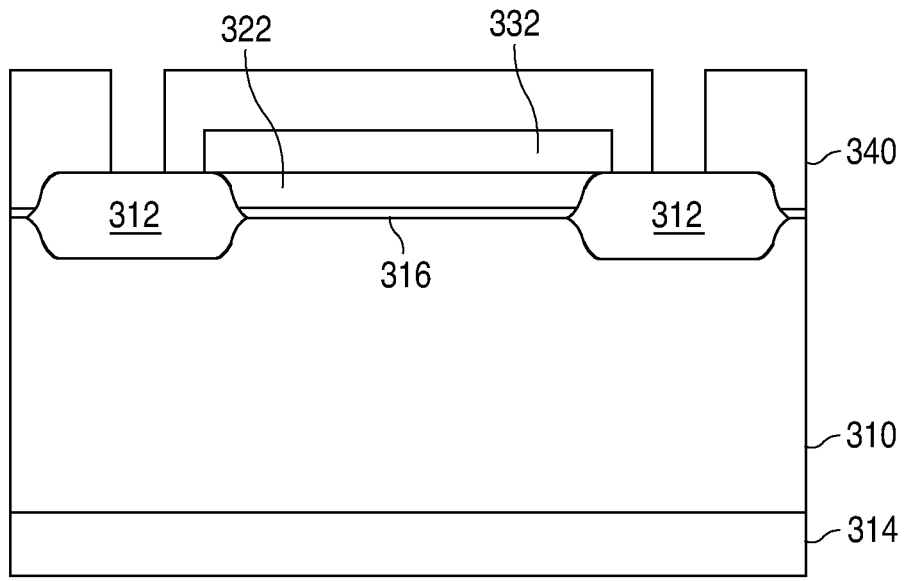
Figure 3H:
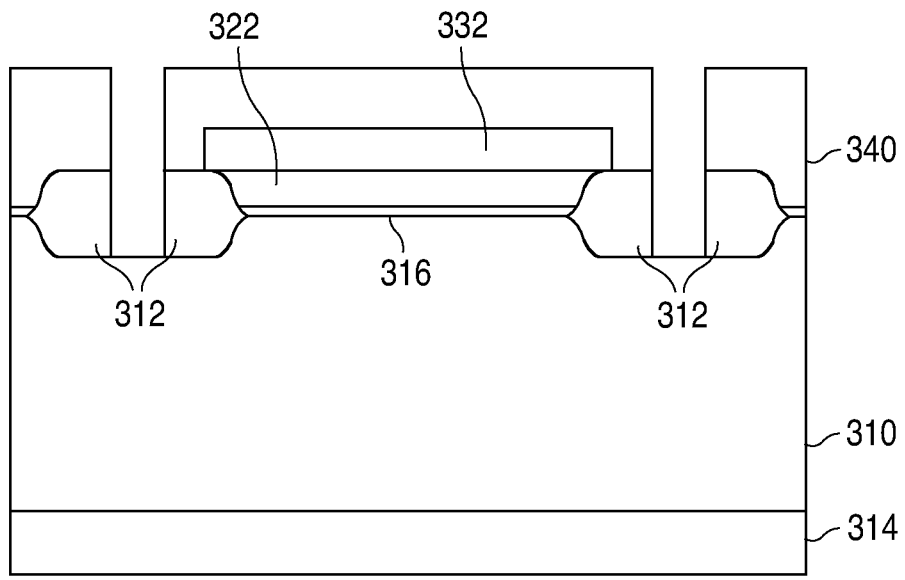
Figure 3I:
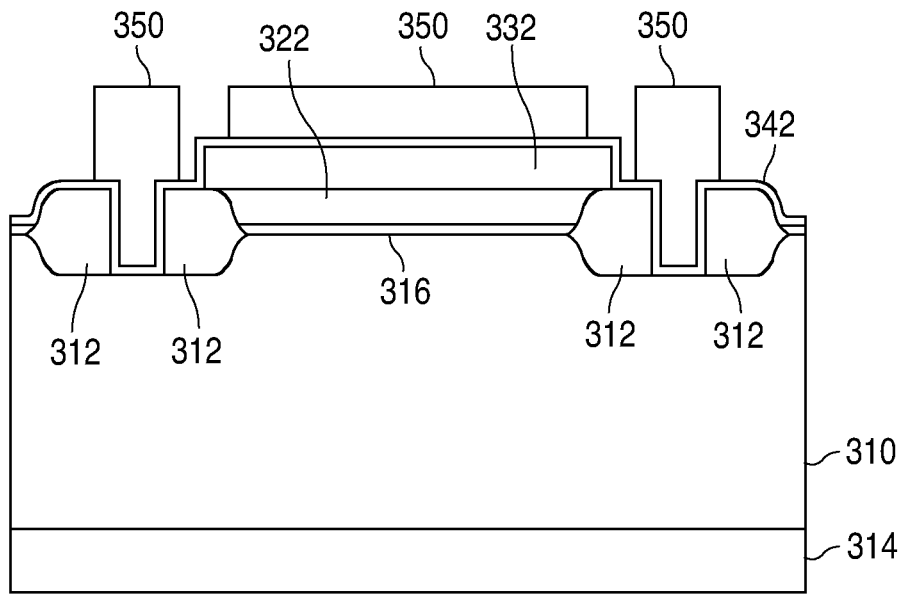
Figure 3J:
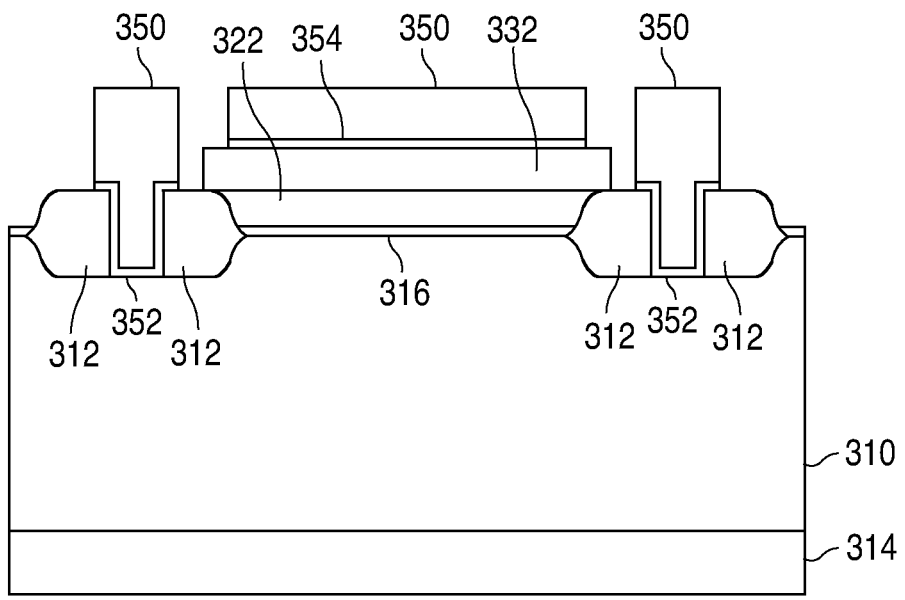
Figure 3K:
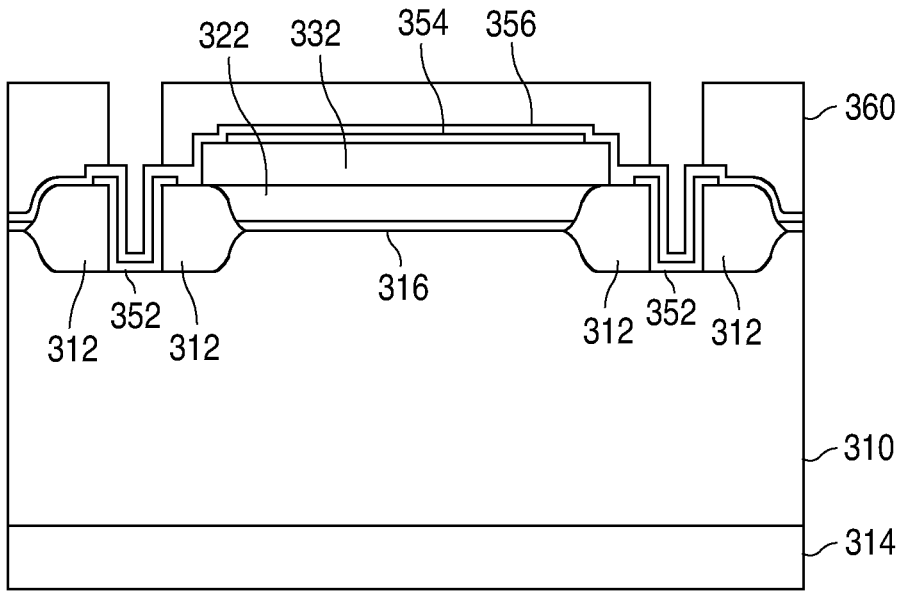
Figure 3L:
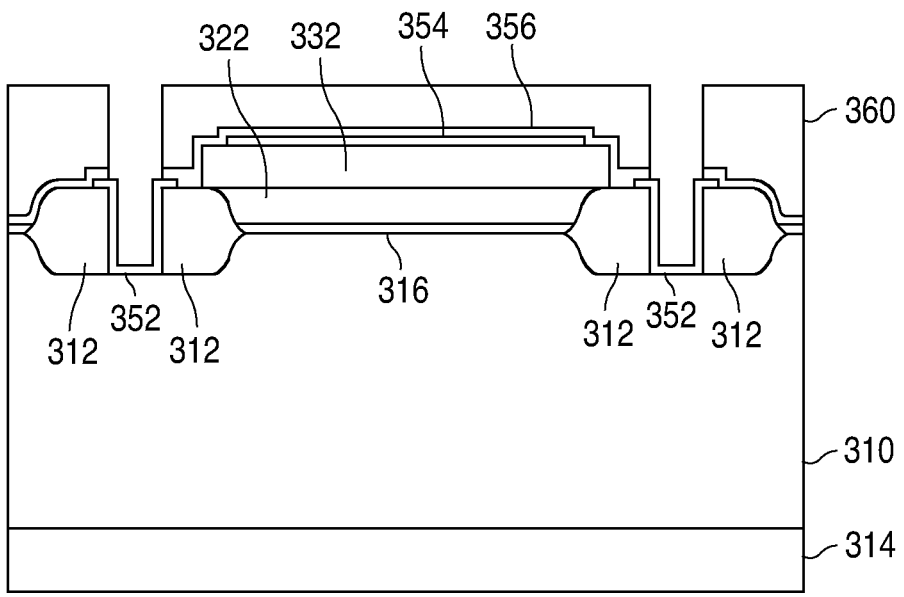
Figure 3M:
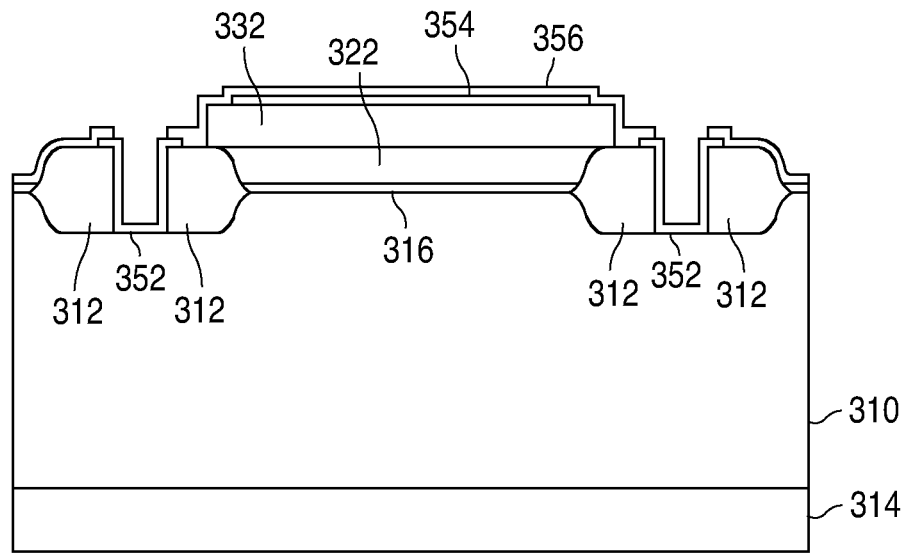
Figure 3N:
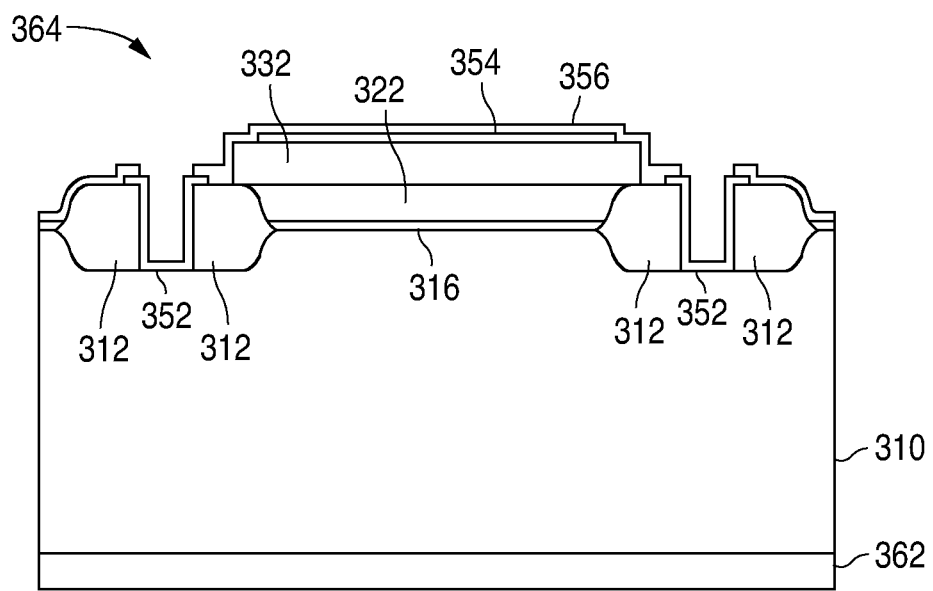
Figure 4A:
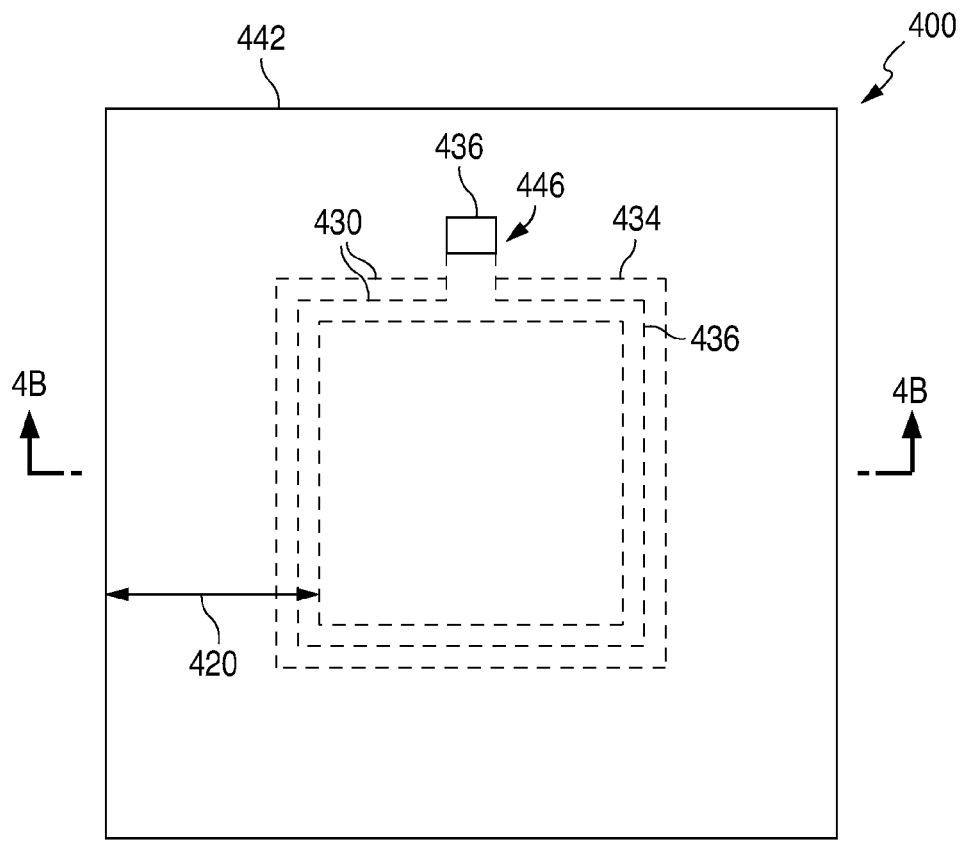
FIGS. 4A-4B are views illustrating an example of a CMUT 400 in accordance with the present invention.
Figure 4B:
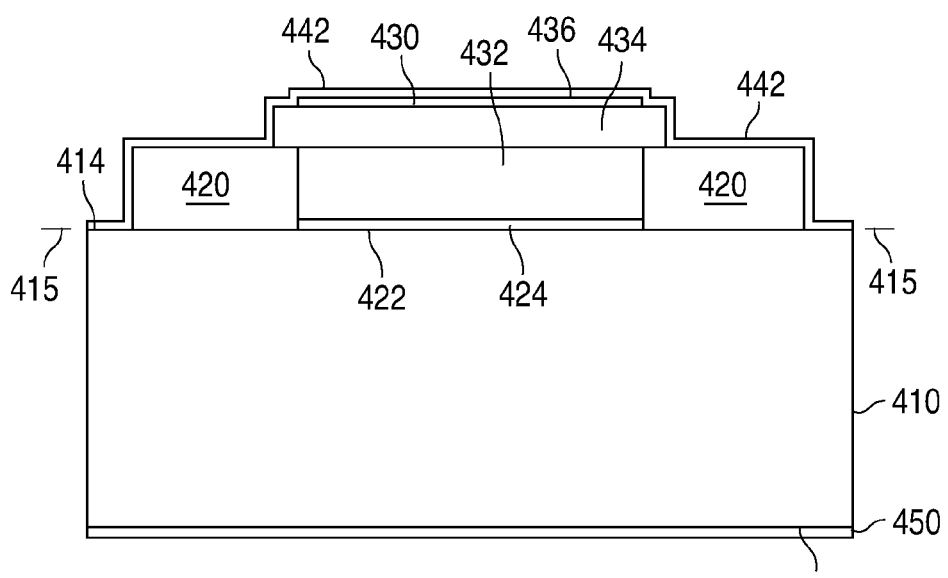

FIGS. 4A-4B show views that illustrate an example of a CMUT 400 in accordance with the present invention. FIG. 4A shows a plan view of CMUT 400, while FIG. 4B shows a cross-sectional view taken along line 4B-4B of FIG. 4A. As described in greater detail below, CMUT 400 utilizes thick oxide to increase the size of the cavity which, in turn, allows the CMUT to receive and transmit low frequency ultrasonic waves.

As shown in FIGS. 4A-4B, CMUT 400 includes a semiconductor substrate 410 that has a bottom surface 412 and a top surface 414, where the top surface 414 lies in a plane 415. Semiconductor substrate 410, which is conductive, can be implemented with, for example, single-crystal silicon.

In addition, CMUT 400 also includes a post structure 420 that touches the top surface 414 of semiconductor substrate 410 such that no portion of post structure 420 lies below plane 415, and no non-conductive region lies below plane 415 and touches the bottom surface of post structure 420. Further, post structure 420, which is non-conductive, laterally surrounds a cell region 422 of the top surface 414 of semiconductor substrate 410. In addition, no conductive structure extends through post structure 420.

As further shown in FIGS. 4A-4B, CMUT 400 includes a non-conductive structure 424 that touches the cell region 422 of the top surface 414 of semiconductor substrate 410. In addition, non-conductive structure 424, which can be implemented with a layer of oxide, is laterally surrounded and touched by post structure 420.

CMUT 400 also includes a conductive structure 430 that touches the top surface of post structure 420, and lies directly vertically over non-conductive structure 424 to form a cavity 432 that lies vertically between non-conductive structure 424 and conductive structure 430. In the present example, conductive structure 430 includes a semiconductor structure 434 such as, for example, single-crystal silicon, and an overlying metal structure 436, such as an aluminum copper plate.

As further shown in FIGS. 4A-4B, CMUT 400 includes a passivation layer 442 that touches and lies over post structure 420 and conductive structure 430. Passivation layer 442, which is non-conductive, has a conductive opening 446 that exposes a region of metal structure 436 that functions as a bond pad. In addition, CMUT 400 includes a metal bond pad structure 450 that touches the bottom surface 412 of semiconductor substrate 410.

In operation, a first bias voltage V1 is placed on semiconductor substrate 410, which functions as a first capacitor plate, and a second bias voltage V2 is placed on conductive structure 430, which functions as second capacitor plate. Thus, the voltage across the capacitor plates lies vertically across cavity 432.

When used as a receiver, an ultrasonic wave causes conductive structure 430 to vibrate. The vibration varies the capacitance across the first and second capacitor plates, thereby generating an electrical signal that varies as the capacitance varies. When used as a transmitter, an alternating electrical signal applied across the biased first and second capacitor plates causes conductive structure 430 to vibrate which, in turn, transmits ultrasonic waves.

One of the advantages of CMUT 400 is that the volume of cavity 432 is substantially greater than the volume of cavity 122 because post structure 420 has a height above the top surface of semiconductor substrate 410 that is significantly larger that the height of post oxide structure 112 above the top surface of semiconductor substrate 110. The increased volume allows CMUT 400 to accommodate the low frequency signals required by ultrasonic airborne imaging applications.

FIGS. 5A-5B show views that illustrate an example of a CMUT array 500 in accordance with the present invention. FIG. 5A shows a plan view of array 500, while FIG. 5B shows a cross-sectional view taken along line 5B-5B of FIG. 5A. As shown in the FIGS. 5A-5B example, CMUT array 500 includes three CMUTS 400 in a single row. In addition, in the present example, laterally adjacent CMUT membranes 434 are separated by 50 μm.

Figure 6A:
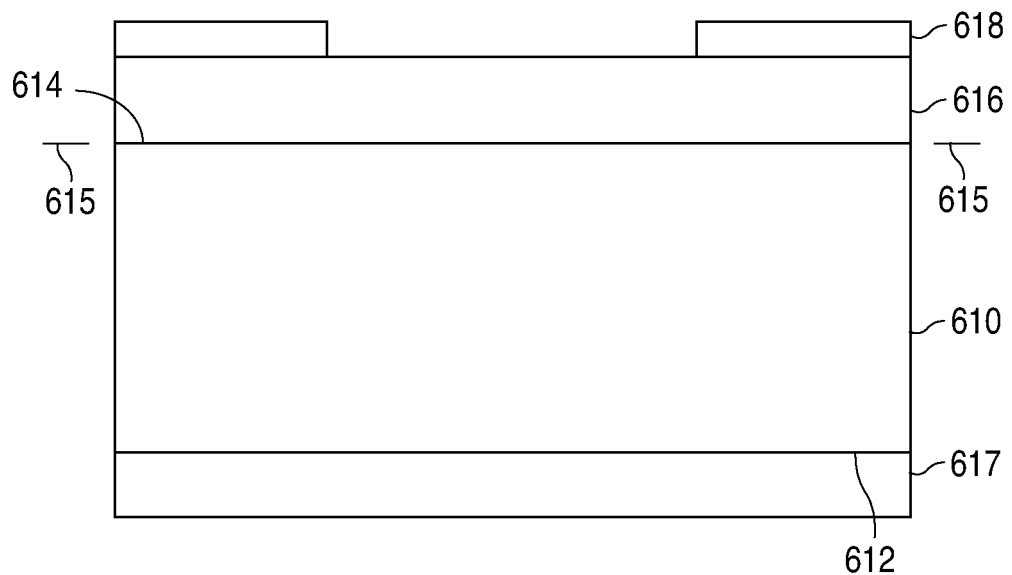
FIGS. 6A-6R are cross-sectional views illustrating an example of a method of forming a CMUT in accordance with the present invention.
Figure 6B:
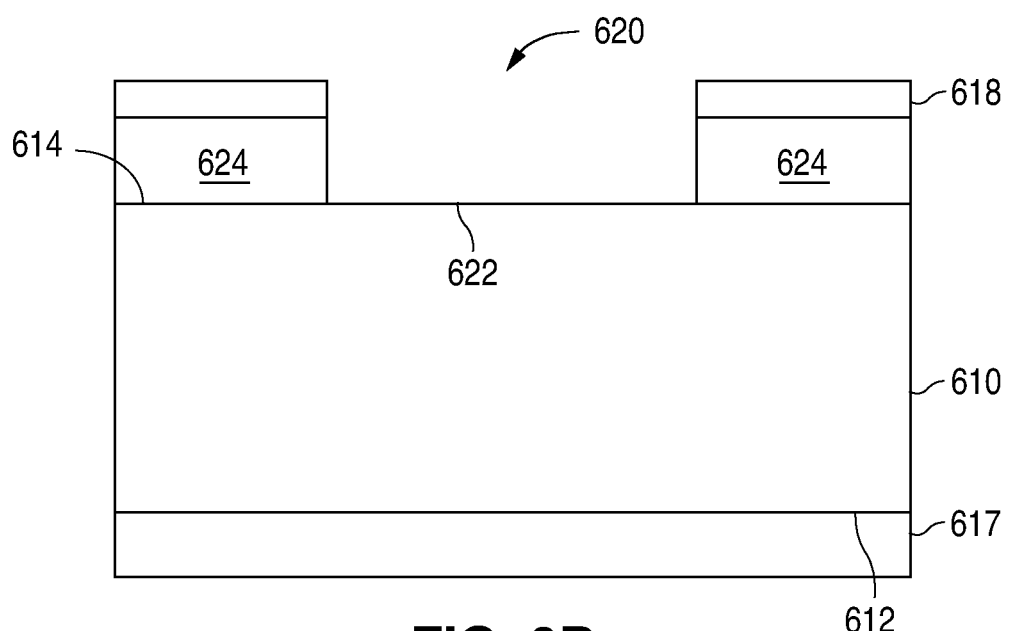
Figure 6C:
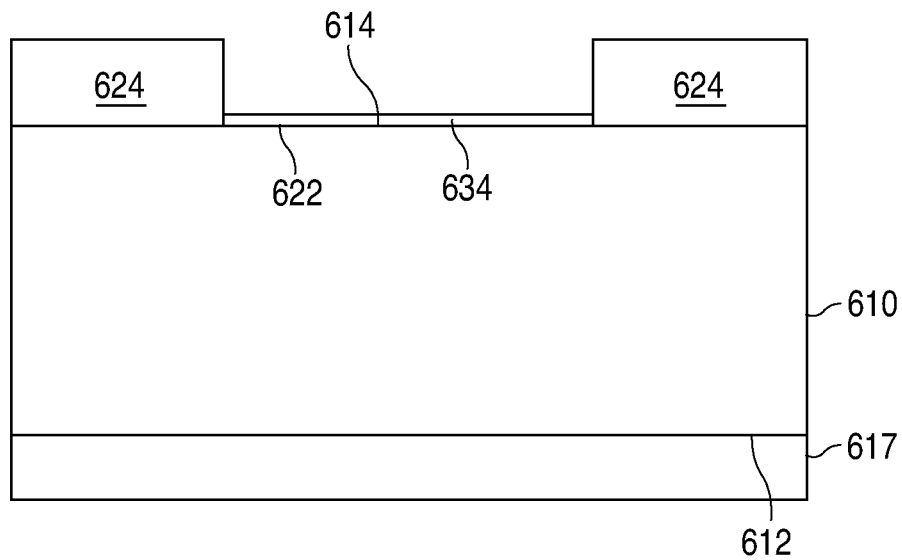
Figure 6D:
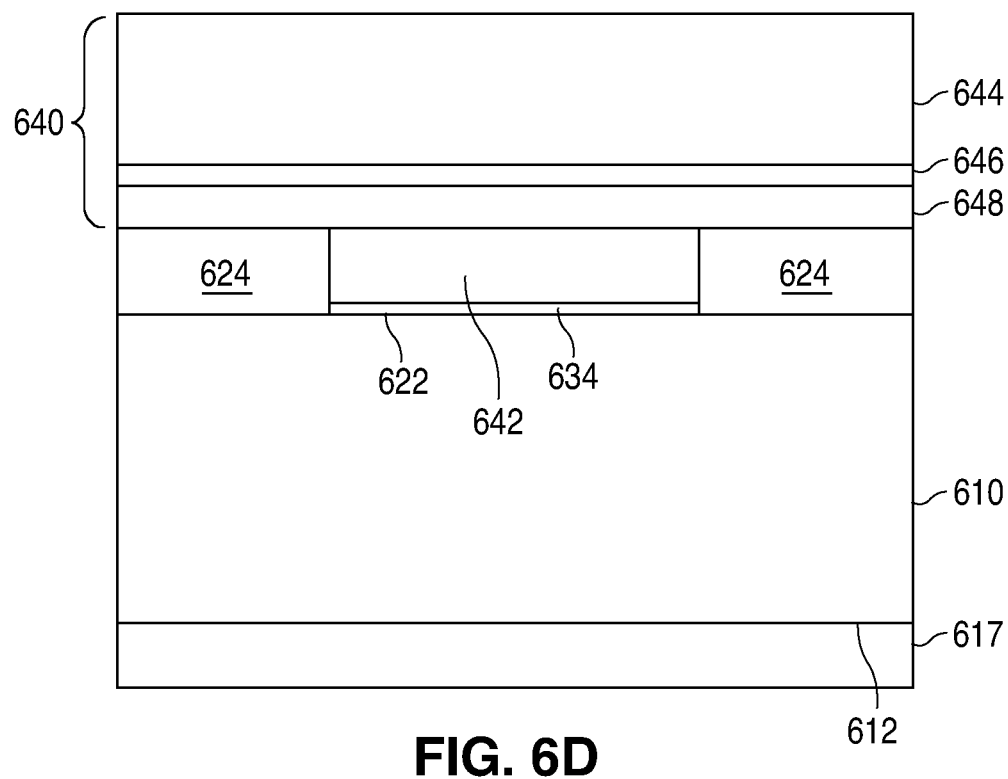
Figure 6E:
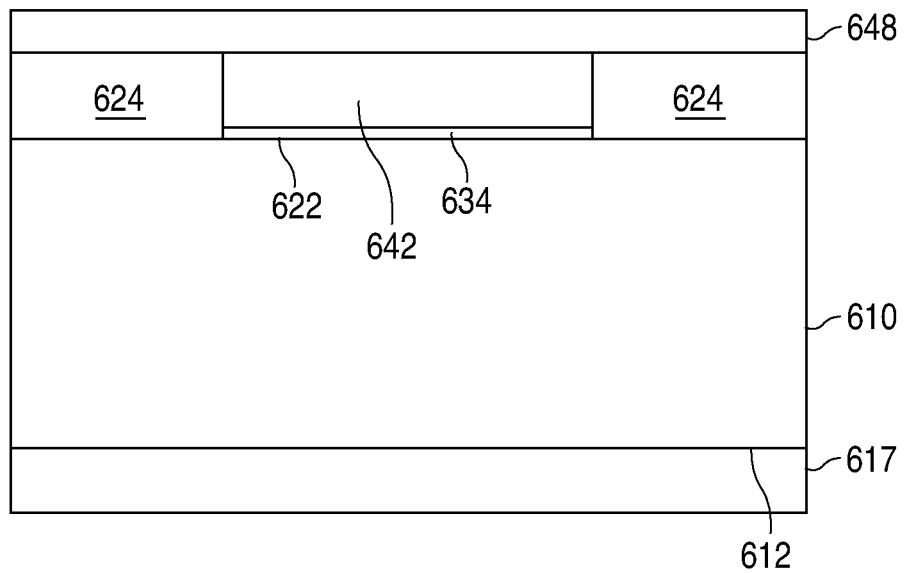
Figure 6F:
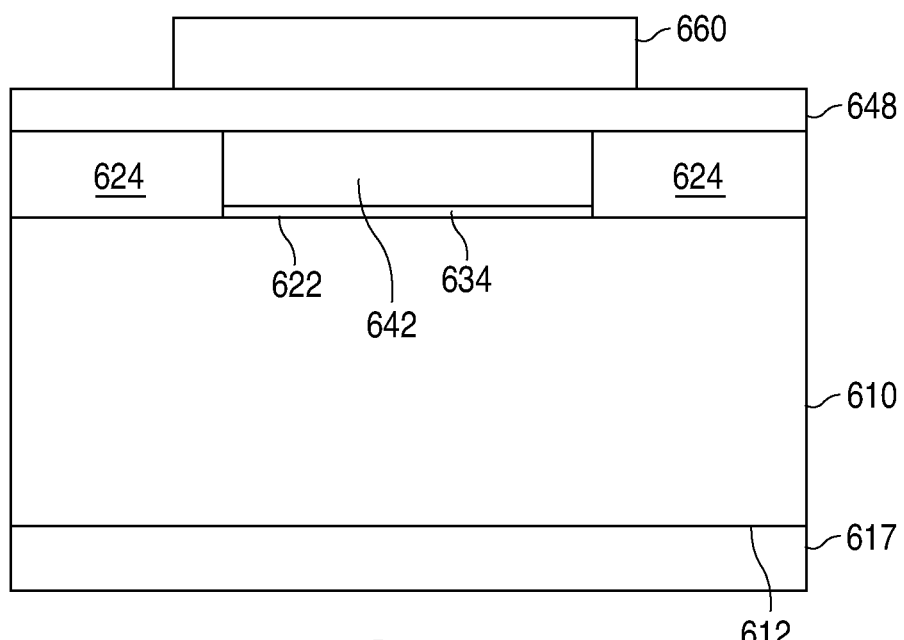
Figure 6G:
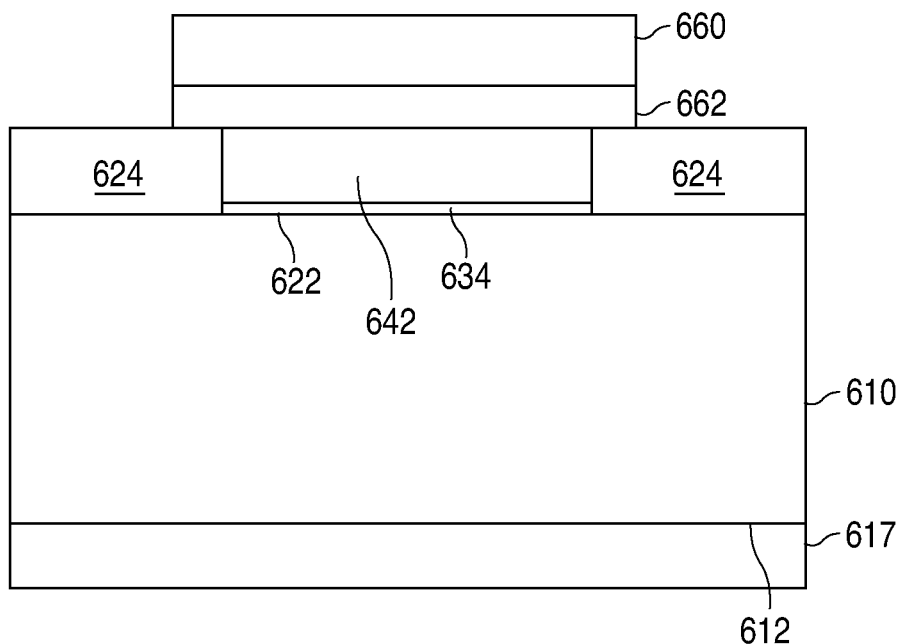
Figure 6H:
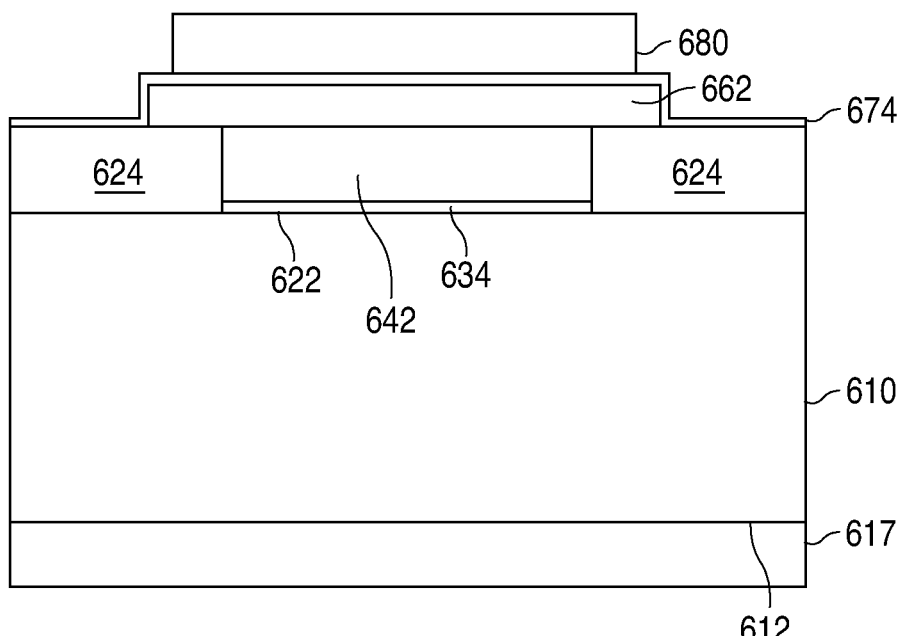
Figure 6I:
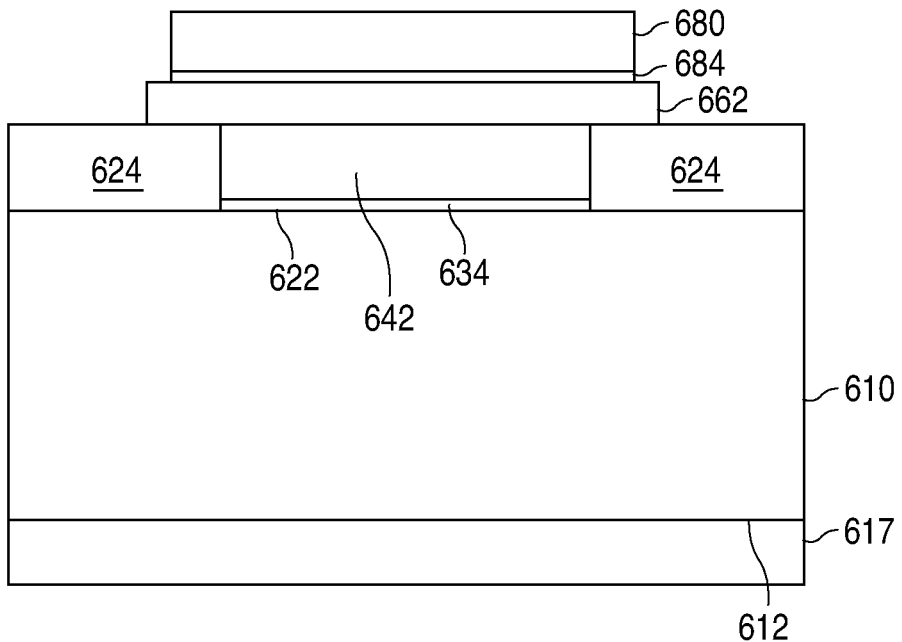
Figure 6J:
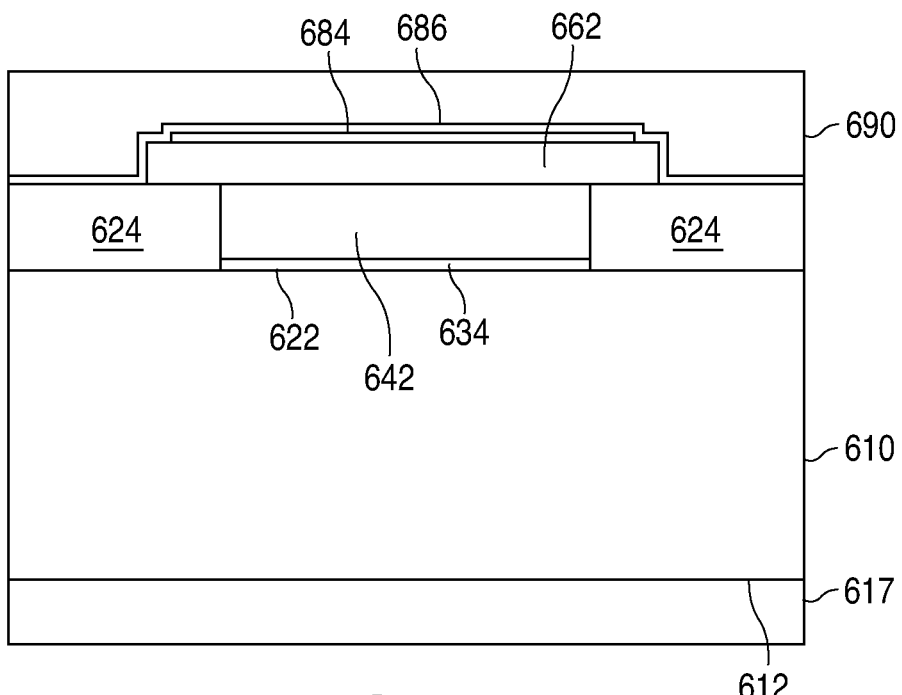
Figure 6K:
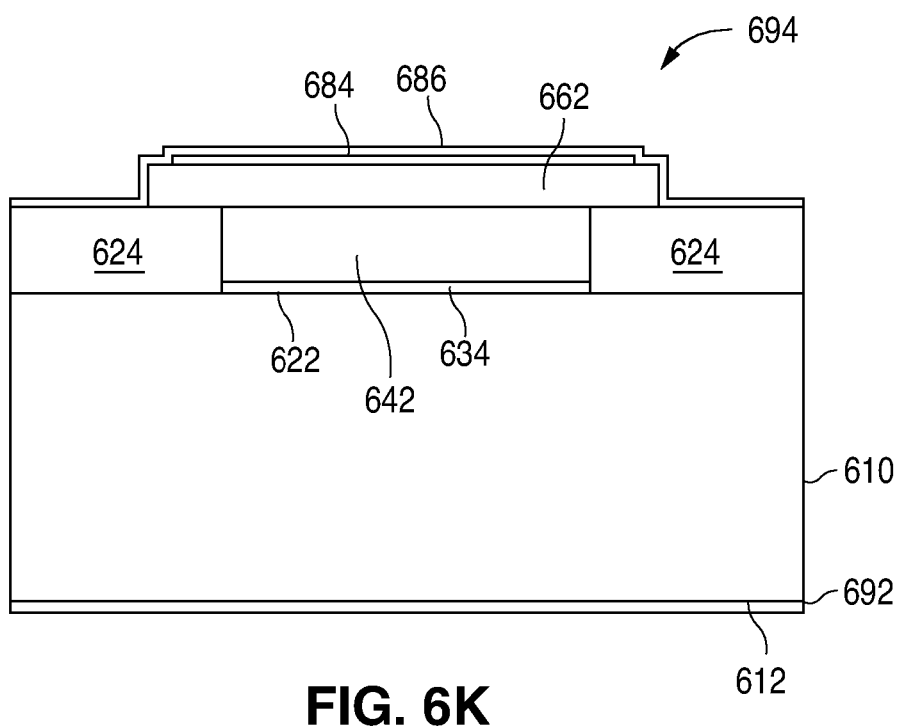
Figure 6L:
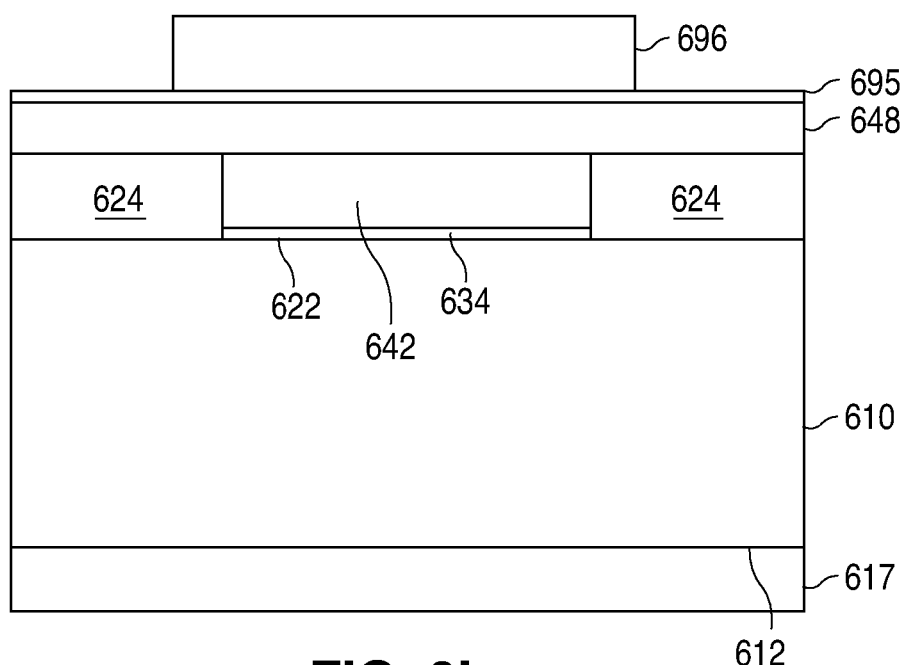
Figure 6M:
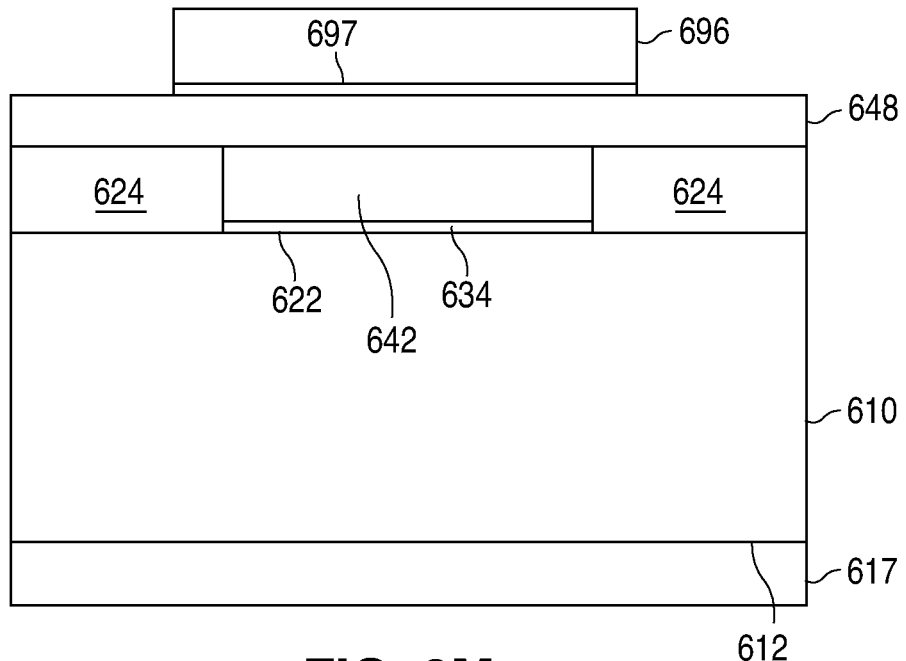
Figure 6N:
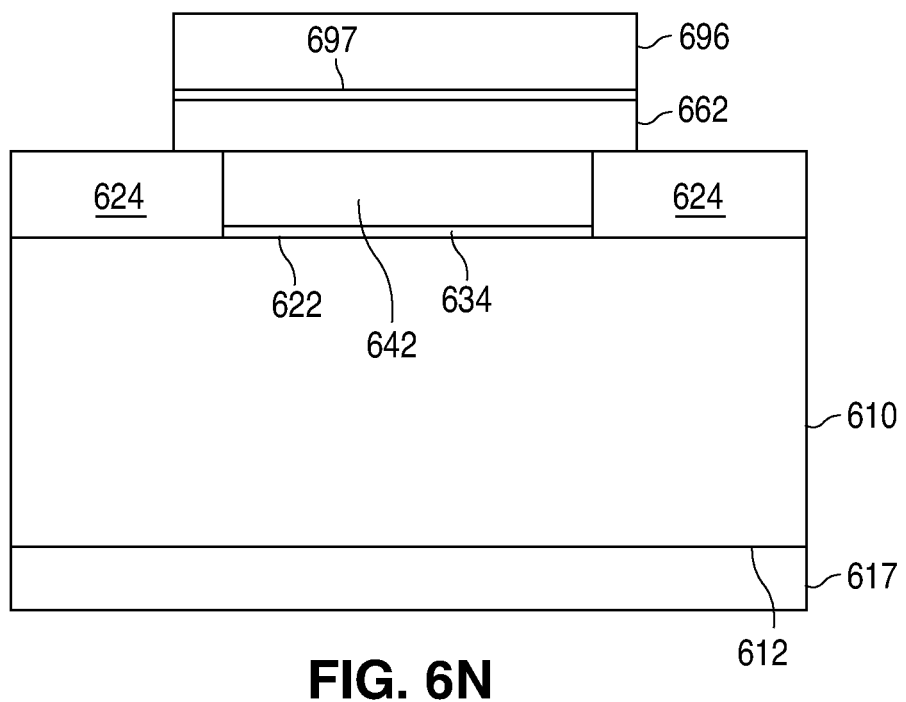
Figure 6O:
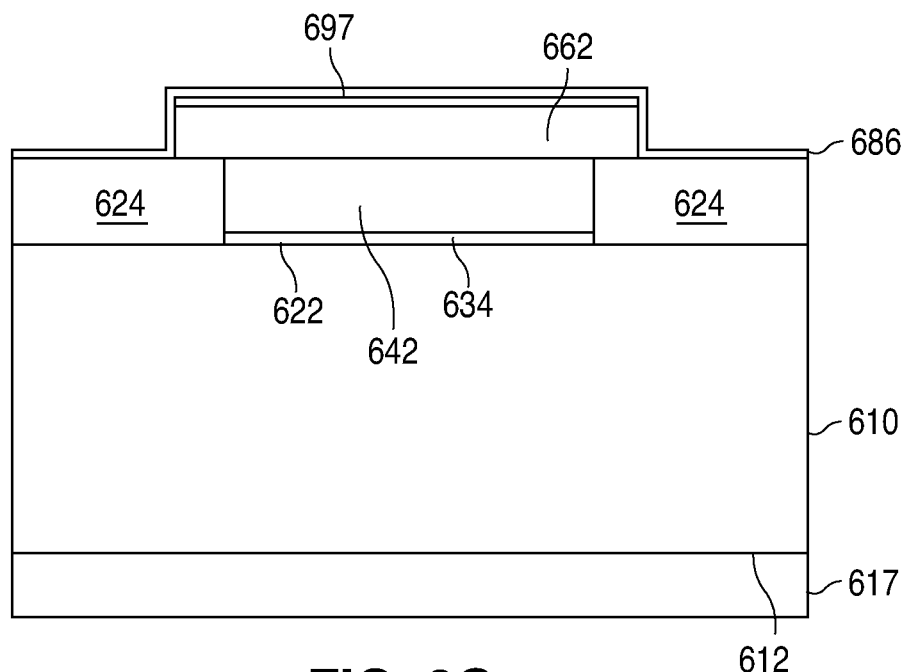
Figure 6P:
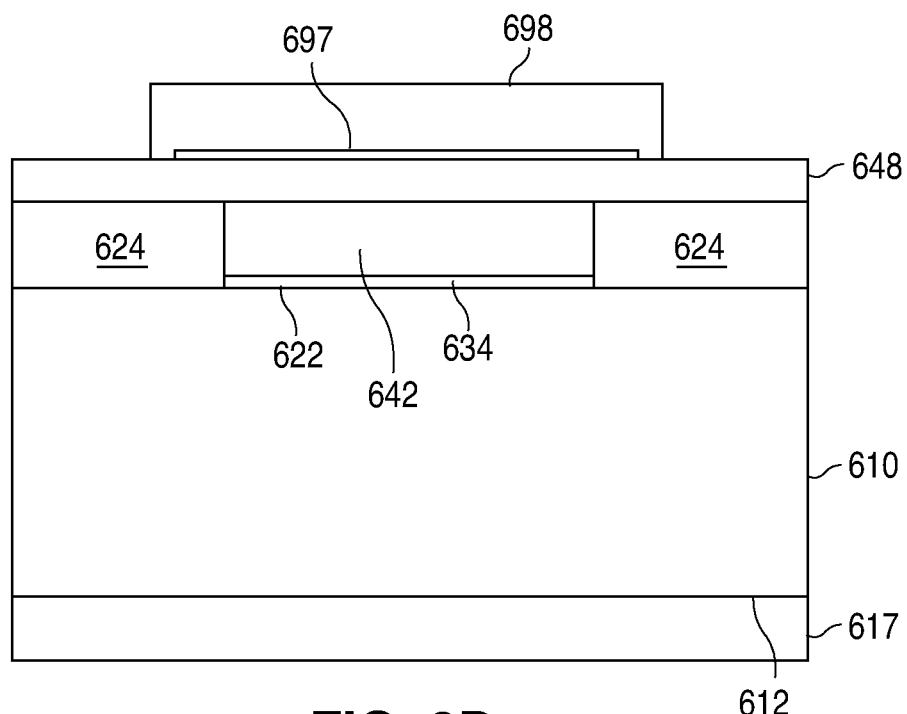
Figure 6Q:
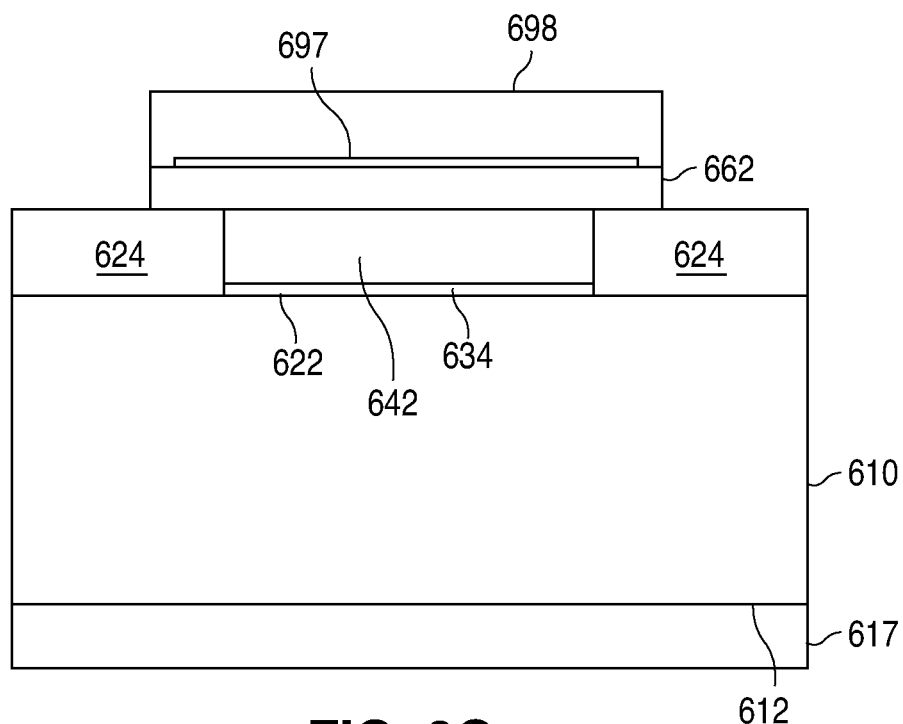
Figure 6R:
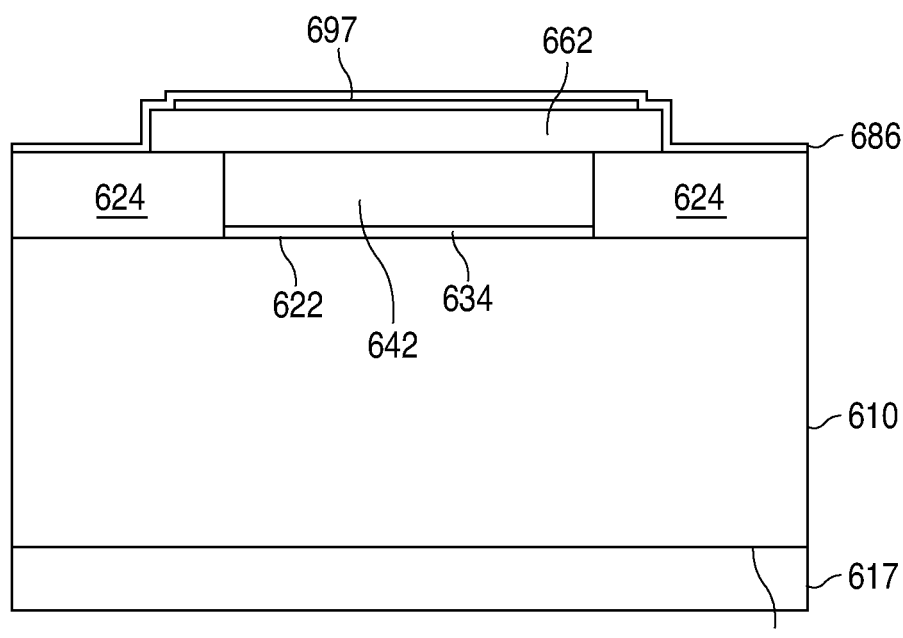

FIGS. 6A-6R show cross-sectional views that illustrate an example of a method of forming a CMUT in accordance with the present invention. As shown in FIG. 6A, the method utilizes a conventionally-formed single-crystal silicon wafer 610 that has a bottom surface 612 and a top surface 614, where the top surface 614 lies in a plane 615. In the present example, silicon wafer 610 has a low resistivity (e.g., 0.1 Ω-cm). Silicon wafer 610 has rows and columns of die-sized regions, and one or more CMUTS can be simultaneously formed in each die-sized region. For simplicity, FIGS. 6A-6R illustrate the formation of a single CMUT.

The method begins by forming a patterned photoresist layer on the top surface 614 of silicon wafer 610 in a conventional manner. After the patterned photoresist layer has been formed, the top surface 614 of silicon wafer 610 is etched for a predefined time to form two or more front side alignment marks.

If a wet etchant is used, the resulting structure is rinsed following the etch. After the rinse, the patterned photoresist layer is conventionally removed, such as with an ash plus a solvent clean. Following the removal of the patterned photoresist layer, the resulting structure is cleaned to remove organics, such as with a Piranha etch (e.g., using a solution of $50H_2SO_4$: $1H_2O_2$ @ 120° C. removes approximately 240 nm/minute).

Next, the method continues by forming a post structure on the top surface 614 of silicon wafer 610. As illustrated in FIG. 6A, the post structure, which is non-conductive, is first formed by growing a thick oxide layer 616 on the top surface 614 of silicon wafer 610 using high-pressure oxidization (HIPOX). In addition, a thick oxide layer 617 is simultaneously grown on the bottom surface 612 of silicon wafer 610.

For example, thick oxide layers 616 and 617 can be grown at a temperature in the range of 900° C. to 1200° C. with an operating pressure of 10 to 20 atm. In the present example, thick oxide layers 616 and 617 are grown to each have a thickness of approximately 5.15 μm. After this, a patterned photoresist layer 618 is formed on thick oxide layer 616 in a conventional manner.

Following the formation of patterned photoresist layer 618, as further shown in FIG. 6B, the exposed region of thick oxide layer 616 is etched to form an opening 620 approximately 1.12 mm wide that exposes a cell region 622 of the top surface 614 of silicon wafer 610, and form a post structure 624.

For example, a non-polymerizing plasma etch can be used to etch an opening through approximately 4.65 μm of the approximately 5.15 μm thick oxide layer 616. In this example, the slope of the side wall at the end of the non-polymerizing etch is approximately 80° (i.e., the opening is slightly larger at the top than at the bottom), and results from the natural erosion of patterned photoresist layer 618.

Following this, the remaining approximately 0.5 μm of thick oxide layer 616 is removed without damaging the cell region 622 of the top surface 614 of silicon wafer 610 using, for example, a wet etchant that is highly or completely selective to silicon. After this, the resulting structure is rinsed, and patterned photoresist layer 618 is conventionally removed, such as with an ash plus a solvent clean. The resulting structure is then subjected to a conventional pre-oxidization clean.

The top surface of thick oxide layer 616, and thereby the top surface of post structure 624, are substantially planar. In addition, the surface roughness of thick oxide layer 616, and thereby the surface roughness of post structure 624, must be controlled to provide a good bonding surface. In the present example, the surface roughness is less than 3 Å RMS.

Following this, as shown in FIG. 6C, a cell oxide layer 634 is grown on the cell region 622 of the top surface 614 of silicon wafer 610 in a conventional manner to have a thickness of, for example, 0.3 μm. After cell oxide layer 634 has been formed, as shown in FIG. 6D, a silicon-on-oxide (SOI) wafer 640 is bonded to the top surface of post structure 624 to form a cavity 642.

In the present example, SOI wafer 640 is vacuum fusion bonded to post structure 624 of silicon wafer 610 in a conventional manner so that cavity 624 has a vacuum, followed by an anneal to ensure reliable bonding strength. The anneal can be performed with a temperature in the range of 400° C. to 1050° C. In the present example, the anneal is performed at 1050° C. immediately after the bonding for approximately four hours. Alternately, other bonding approaches can also be used.

SOI wafer 640 has a handle wafer 644, an insulation layer 646 that touches handle wafer 644, and a single-crystal silicon substrate structure 648. Substrate structure 648, in turn, has a first substantially-planar surface that touches insulation layer 646, and a second substantially-planar surface that touches post structure 624. In the present example, insulation layer 646 has a thickness of 1.1 μm, and substrate structure 648 has a thickness of 14 μm.

As shown in FIG. 6E, after substrate structure 648 has been bonded to post structure 624, handle wafer 644 is removed in a conventional manner. For example, handle wafer 644 can be removed by first grinding handle wafer 644 down to a thickness of approximately 150 μm. In the present example, a four hour anneal at 1050° C. is next performed, followed by a wet etch, such as with a solution of KOH or TMAH, to remove the remainder of handle wafer 644.

After handle wafer 644 has been removed, insulation layer 646 is removed in a conventional manner. For example, insulation layer 646 can be removed using a wet HF etchant that is highly selective to silicon, or chemical mechanical polishing. The wet etch of insulation layer 646 could be performed using a single-sided wet etch, such as a SEZ etch by SEZ Austria GmbH, Draubodenweg 29, A-9500 Villach, Austria.

Once insulation layer 646 has been removed, the center region of substrate structure 648 is pulled towards the bottom surface of cavity 642 by approximately 4 μm due to the vacuum in cavity 642 and the effects of atmospheric pressure. To avoid the possibility that substrate structure 648 could be bonded to the top surface of non-conductive structure 634 during the second four hour anneal, the second four hour anneal is performed prior to the wet etch of the final 150 μm Si substrate remaining after the initial back grind process step, and the subsequent wet etch of insulation layer 646.

Following the removal of insulation layer 646, a patterned photoresist layer is formed on the first surface of substrate structure 648 in a conventional manner. Once the patterned photoresist layer has been formed, the exposed regions of substrate structure 648 are etched, such as with a plasma etch, to expose the alignment marks.

Alternately, a conventional Bosch etch can be used to expose the alignment marks. Since post structure 624 (which is approximately 5.15 μm thick and lies over the alignment marks) is transparent, only substrate structure 648, which is approximately 14 μm thick, needs to be removed. After the etch, the patterned photoresist layer is conventionally removed, such as with an ash plus a solvent. Following the removal of the patterned photoresist layer, the resulting structure is cleaned to remove organics, such as with a Piranha etch.

As shown in FIG. 6F, after cleaning following the removal of the patterned photoresist layer used to expose the alignment marks, a patterned photoresist layer 660 is formed on the first surface of substrate structure 648 in a conventional manner. Once patterned photoresist layer 660 has been formed, as shown in FIG. 6G, the exposed regions of substrate structure 648 are etched to form a CMUT membrane 662 that lies directly vertically over the cell region 622 of the top surface 414 of silicon wafer 610.

For example, a conventional Bosch etch with a short Bosch cycle to minimize side wall scalloping can be used to pattern CMUT membrane 662 without damaging CMUT membrane 662. After the etch, patterned photoresist layer 660 is conventionally removed, such as with an ash plus a solvent clean. Following the removal of patterned photoresist layer 660, the resulting structure is cleaned to remove organics, such as with a Piranha etch.

As shown in FIG. 6H, after cleaning following the removal of patterned photoresist layer 660, a metal layer 674, such as a layer of aluminum copper, is deposited to touch post structure 624 and CMUT membrane 662. In the present example, metal layer 674 is formed to have a thickness of 1 μm. Next, a patterned photoresist layer 680 is formed on metal layer 674 in a conventional manner.

As shown in FIG. 6I, after patterned photoresist layer 680 has been formed, the exposed region of metal layer 674 is wet etched to form a metal plate 684 that touches the top surface of CMUT membrane 662. In the present example, metal plate 684 has a minimum width of approximately 50 μm. Following the etch, the resulting structure is rinsed. After the rinse, patterned photoresist layer 680 is conventionally removed, such as with an ash plus a solvent clean.

After cleaning following the removal of patterned photoresist layer 680, as shown in FIG. 6J, a passivation layer 686, such as a layer of plasma oxide approximately 0.6 μm thick and an overlying layer of plasma nitride approximately 0.6 μm thick, is deposited on post structure 624, CMUT membrane 662, and metal plate 684. Next, a patterned photoresist layer 690 is formed on passivation layer 686 in a conventional manner.

After patterned photoresist layer 690 has been formed, the exposed region of passivation layer 686 is wet etched to form an opening, like opening 446 shown in FIG. 4A, that exposes a bond pad region on metal plate 684. Following the etch, the resulting structure is rinsed. After the rinse, patterned photoresist layer 690 is conventionally removed, such as with an ash plus a solvent clean. In the present example, after the removal of patterned photoresist layer 690, the resulting structure is alloyed at, for example, 400° C. in an ambient of $N_2 + H_2$.

Next, as shown in FIG. 6K, the resulting structure is flipped over for processing, and thick oxide layer 617 is removed in a conventional manner. For example, thick oxide layer 617 can be removed using chemical mechanical polishing. Alternately, thick oxide layer 617 can be removed using a single-sided wet etch, such as a SEZ etch.

Following the removal of thick oxide layer 617, a metal layer 692, such as 100 Å of titanium and 1 μm of aluminum copper, is deposited onto the bottom surface 612 of silicon wafer 610 to form a CMUT 694. Metal layer 692 can also be implemented with other common back side metallization stacks, such as TiNiAg, TiNiAu, CRAu, or TiAu. Silicon wafer 610 is then diced to form a number of individual die that each has one or more CMUTS 694.

In an alternate method, as shown in FIG. 6L, after the removal of insulation layer 646 and prior to the formation of patterned photoresist layer 660, a metal layer 695, such as a layer of aluminum copper, is deposited to touch the top surface of substrate structure 648. In the present example, metal layer 695 is formed to have a thickness of 1 μm. Next, a patterned photoresist layer 696 is formed on metal layer 695 in a conventional manner.

As shown in FIG. 6M, after patterned photoresist layer 696 has been formed, the exposed region of metal layer 695 is wet etched to form a metal plate 697 that touches the top surface of substrate structure 648. In the present example, metal plate 697 has a minimum width of approximately 50 μm. Following the etch, the resulting structure is rinsed.

In a first variation, as shown in FIG. 6N, after the rinse, the exposed regions of substrate structure 648 are next etched to form CMUT membrane 662. After the etch has been completed, patterned photoresist layer 696 is conventionally removed, such as with an ash plus a solvent clean.

As shown in FIG. 6O, following the removal of patterned photoresist layer 696, the method continues as described above with the formation of passivation layer 686, except that passivation layer 686 is formed on metal plate 697 rather than metal plate 684. One advantage of the first variation is that the first variation eliminates one masking step. However, a dedicated silicon etch tool may be required to etch silicon with the exposed aluminum copper of metal plate 697.

In a second variation, as shown in FIG. 6P, following the formation of metal plate 697, the resulting structure is rinsed. After the rinse, patterned photoresist layer 696 is conventionally removed, such as with an ash plus a solvent clean. Following the removal of patterned photoresist layer 696, a patterned photoresist layer 698 is formed on substrate structure 648 and metal plate 697 in a conventional manner.

As shown in FIG. 6Q, after patterned photoresist layer 698 has been formed, the exposed region of substrate structure 648 is etched to form CMUT membrane 662. Following the etch, the resulting structure is rinsed. After the rinse, patterned photoresist layer 698 is conventionally removed, such as with an ash plus a solvent clean.

As shown in FIG. 6R, following the removal of patterned photoresist layer 698, the method continues as described above with the formation of passivation layer 686, except that passivation layer 686 is formed on metal plate 697 rather than metal plate 684. One advantage of the second variation is that step coverage issues associated with depositing aluminum copper and a patterned photoresist layer over the 14 µm step of patterned CMUT membrane 662 are eliminated.

Figure 7A:
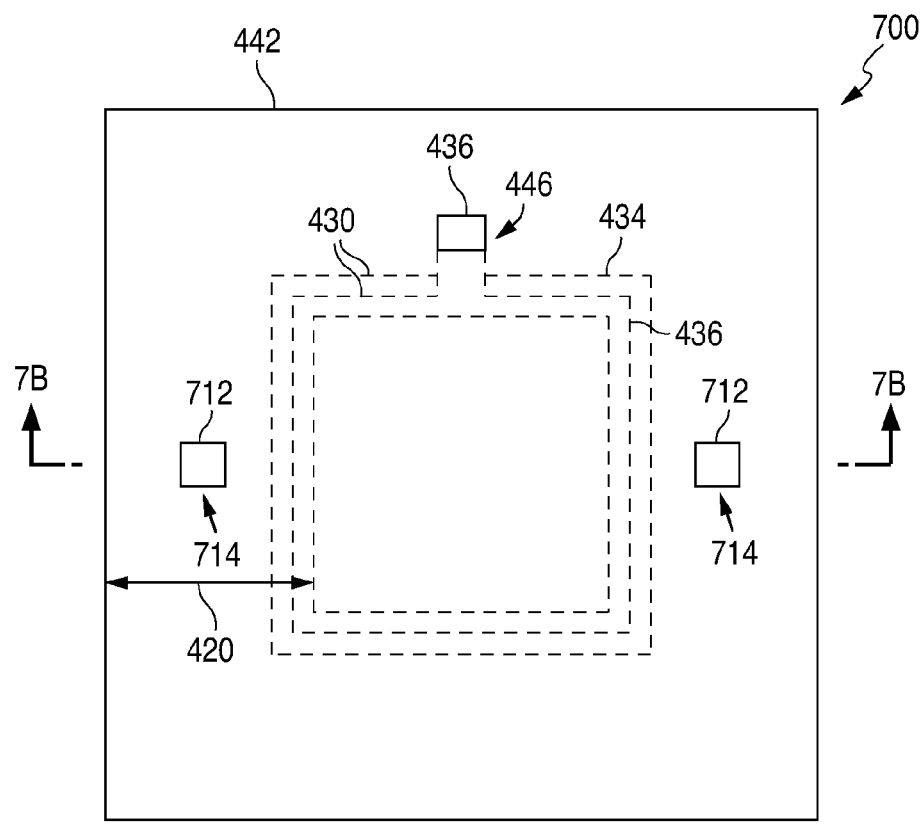
FIGS. 7A-7B are views illustrating an example of a CMUT 700 in accordance with an alternate embodiment of the present invention.
Figure 7B:
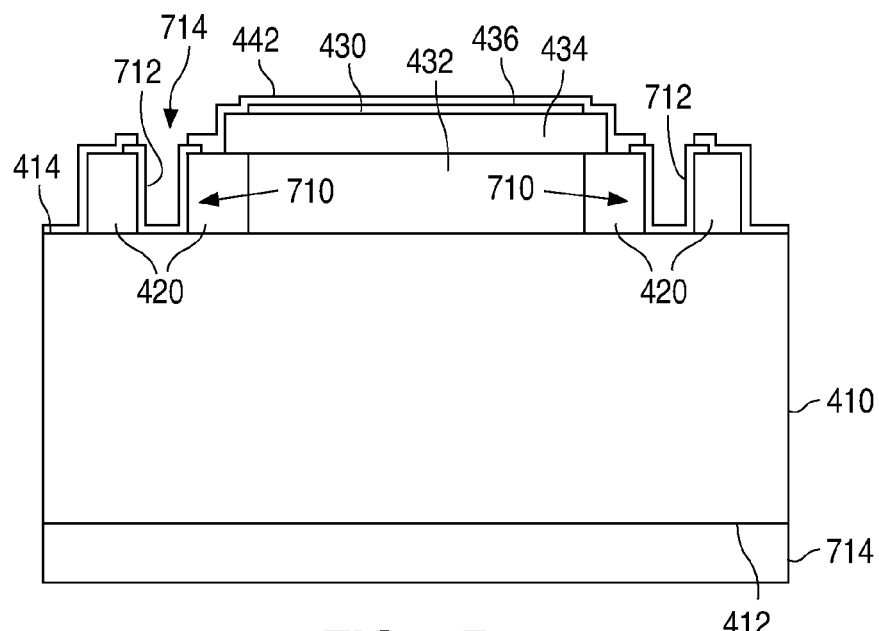

FIGS. 7A-7B show views that illustrate an example of a CMUT 700 in accordance with an alternate embodiment of the present invention. FIG. 7A shows a plan view of CMUT 700. FIG. 7B shows a cross-sectional view taken along line 7B-7B of FIG. 7A. CMUT 700 is similar to CMUT 400 and, as a result, utilizes the same reference numerals to designate the elements which are common to both CMUTS.

As shown in FIGS. 7A-7B, CMUT 700 differs from CMUT 400 in that post structure 420 of CMUT 700 includes substrate contact openings 710 that extend completely through post structure 420 to expose semiconductor substrate 410. In addition, CMUT 700 includes substrate bond pads 712 that lie within the substrate contact openings 710 to make electrical connections to semiconductor substrate 410. Further, passivation layer 442 of CMUT 700 has openings 714 that expose the substrate bond pads 712.

In addition, CMUT 700 includes a backside structure 714 that touches the bottom side 412 of semiconductor substrate 410. Backside oxide structure 710, which is non-conductive and can optionally be removed in the same manner that thick oxide layer 617 is removed, is formed automatically at the same time that post structure 420 is formed.

Figure 8A:
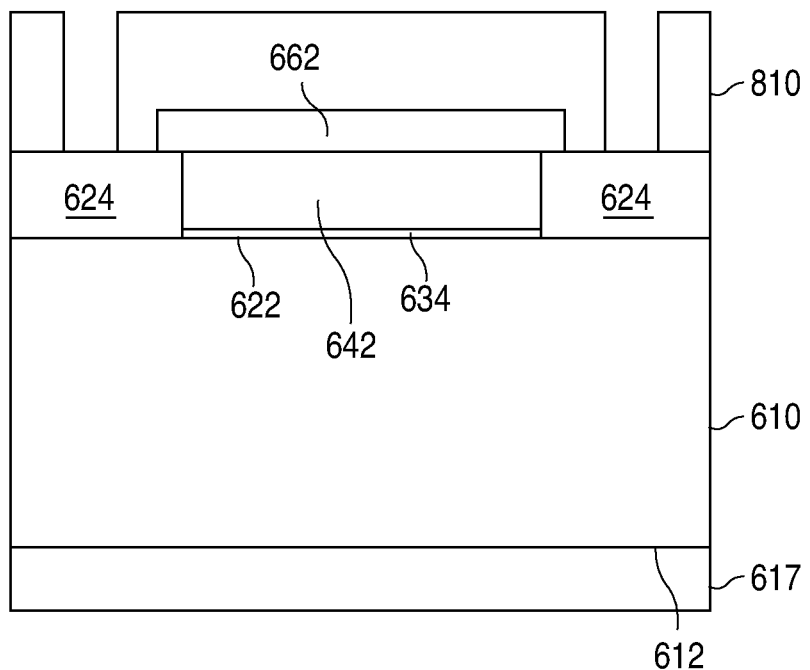
FIGS. 8A-8D are cross-sectional views illustrating an example of a method of forming a CMUT in accordance with an alternate embodiment of the present invention.

FIGS. 8A-8D are cross-sectional views illustrating an example of a method of forming a CMUT in accordance with an alternate embodiment of the present invention. The present method is the same as the method illustrated in FIGS. 6A-6G, up through the removal of patterned photoresist layer 660. As shown in FIG. 8A, after the cleaning following the removal of patterned photoresist layer 660, a patterned photoresist layer 810 is formed on post structure 624 and CMUT membrate 662 in a conventional manner.

Figure 8B:
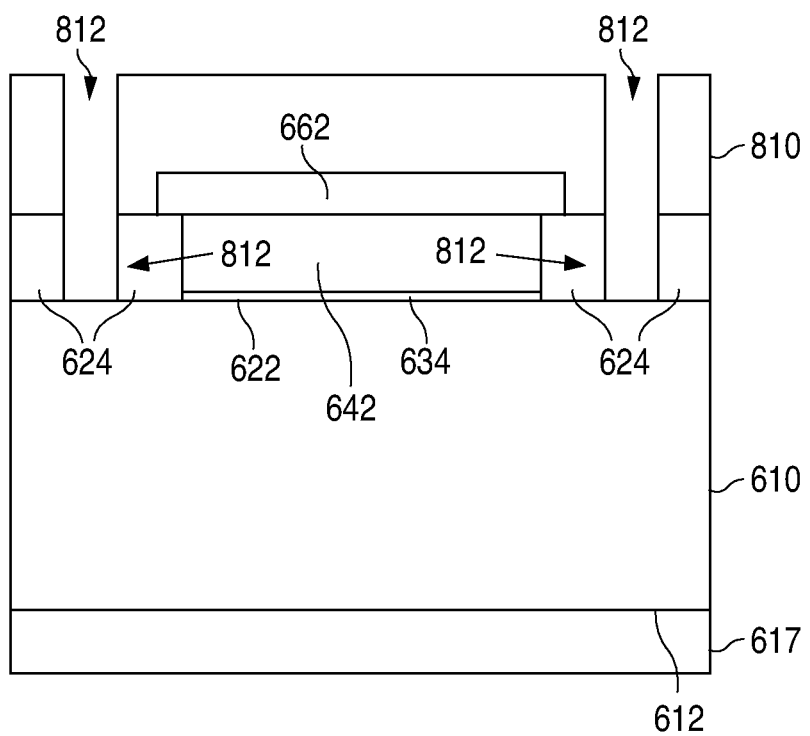

Once patterned photoresist layer 810 has been formed, as shown in FIG. 8B, the exposed regions of post structure 624 are etched to form substrate contact openings 812 that expose silicon wafer 610. In the present example, the substrate contact openings 812 each has a diameter of 50 µm. If a wet etchant is used, the resulting structure is rinsed following the etch. After the rinse, patterned photoresist layer 810 is conventionally removed, such as with acetone. Following the removal of patterned photoresist layer 810, the resulting structure is cleaned to remove organics, such as with a Piranha etch.

Figure 8C:
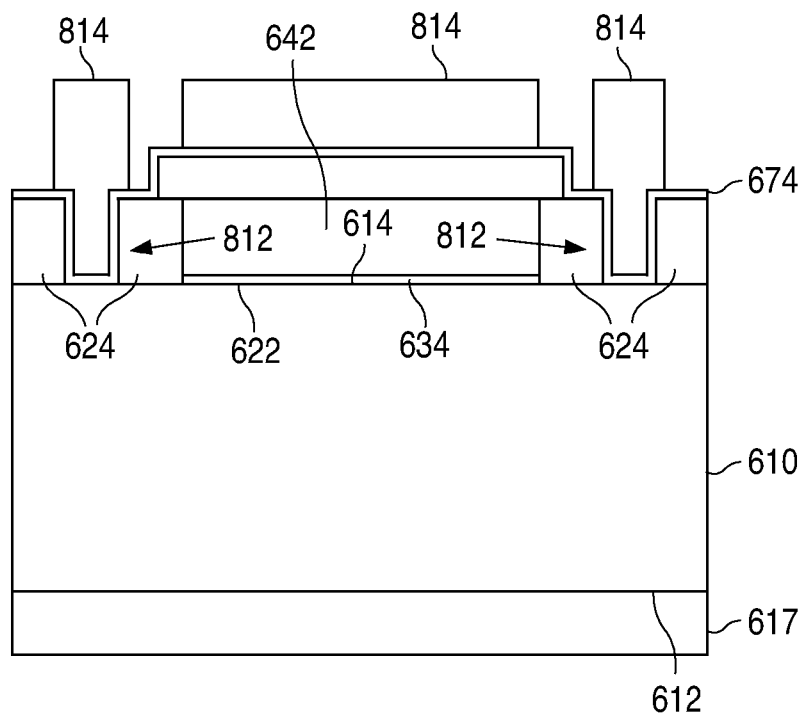

As shown in FIG. 8C, after cleaning following the removal of patterned photoresist layer 810, metal layer 674 is deposited as before to touch post structure 624 and CMUT membrane 662, and now also lines the openings 812 to touch the top surface 614 of silicon wafer 610. Next, a patterned photoresist layer 814 is formed on metal layer 674 in lieu of patterned photoresist layer 680.

Figure 8D:
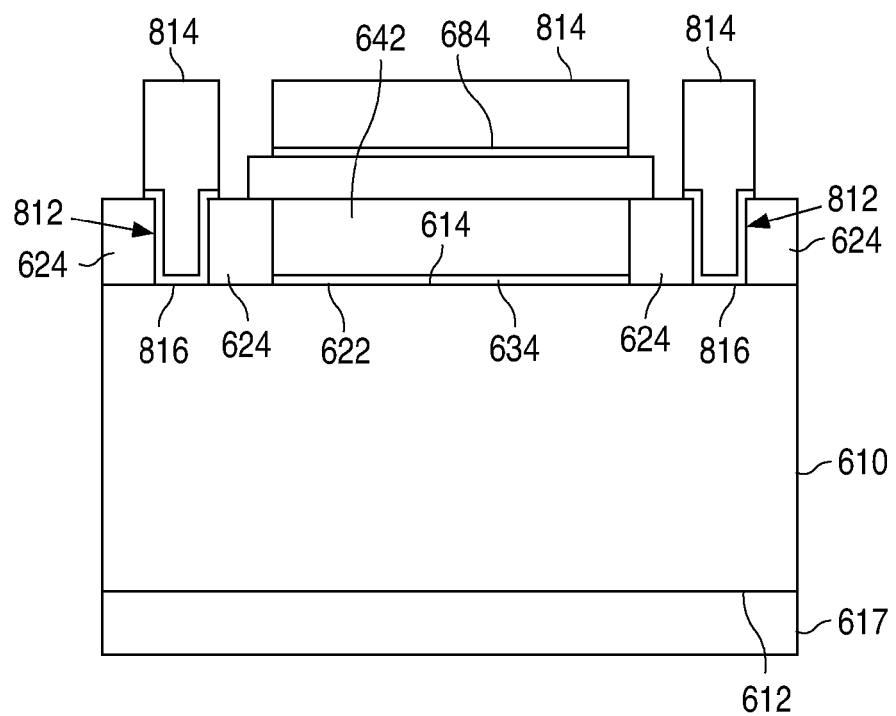

As shown in FIG. 8D, after patterned photoresist layer 814 has been formed, the exposed region of metal layer 674 is wet etched to form metal plate 684 as before, and also form substrate bond pads 816 that lie within the substrate contact openings 812 to make electrical connections to silicon substrate 610.

Following the etch, the resulting structure is rinsed. After the rinse, patterned photoresist layer 814 is conventionally removed, such as with acetone. After the removal of patterned photoresist layer 814, the method continues as before with the formation of passivation layer 686, except that openings are also formed in passivation layer 686 to expose the substrate bond pads 816 as the same time that the opening, like opening 446 in FIG. 4A, is formed to expose the bond pad region on metal plate 684. In addition, the formation of bond pad structure 692 is omitted, and the removal of thick oxide layer 617 is optionally omitted.

It should be understood that the above descriptions are examples of the present invention, and that various alternatives of the invention described herein may be employed in practicing the invention. Thus, it is intended that the following claims define the scope of the invention and that structures and methods within the scope of these claims and their equivalents be covered thereby.

What is claimed is:
1. A method of forming a semiconductor transducer comprising:
   providing semiconductor substrate having top and bottom surfaces wherein the top surface lies in a plane;
   growing approximately a 5.15 micrometer thick oxide layer on both the top and bottom surfaces of the semiconductor wafer using a high-pressure oxidation (HIPOX) process;
   wherein the 5.15 micrometer thick oxide layer is grown at a temperature in range of 900° C. to 1200° C. with an operating pressure of 10 to 20 atmospheres;
   forming a patterned photoresist layer on the thick oxide layer on the top surface of the semiconductor substrate;
   etching the thick oxide layer, exposing the top surface of the semiconductor substrate and forming a post structure on the top surface of the semiconductor substrate from the thick oxide layer, wherein the post structure having a top surface, being non-conductive, and laterally surrounding a cell region of the top surface of the substrate has no portion of the post structure lying below the plane of the top surface of the semiconductor substrate;
   wherein etching the thick oxide layer comprises:
      etching approximately 4.65 micrometers of the approximately 5.15 micrometer thick layer utilizing a non-polymerizing plasma etch, wherein the slope of the side wall at the end of the non-polymerizing etch is approximately 80°, making the opening slightly larger at the top than at the bottom of the thick oxide layer; and
      removing the remaining approximately 0.5 micrometers of the thick oxide layer with a wet etchant that is highly or completely selective to silicon, thus leaving the cell region on the top surface of the semiconductor substrate without damage;

forming a non-conductive structure that touches the cell region of the top surface of the semiconductor substrate; and forming a conductive structure that touches the top surface of the post structure and lies directly vertically over the non-conductive structure to form a cavity that lies vertically between the non-conductive structure and the conductive structure.

2. The method of claim 1 wherein the post structure laterally surrounds and touches the non-conductive structure.

3. The method of claim 2 wherein the cavity is under a vacuum.

4. The method of claim 3 and further comprising forming a metal bond pad structure that touches the bottom surface of the substrate.

5. The method of claim 4 wherein no conductive structure extends through the post structure.

6. The method of claim 5 wherein the conductive structure includes:

a single-crystal silicon structure; and a metal plate that touches the single-crystal silicon structure.

7. The method of claim 3 and further comprising forming a bond pad opening that extends completely through the post structure to expose the substrate.

8. The method of claim 7 and further comprising forming a conductive bond pad structure that lies in the bond pad opening to touch the substrate.

9. The method of claim 8 wherein the conductive structure includes:

a single-crystal silicon structure; and a metal plate that touches the single-crystal silicon structure.

10. The method of claim 2 wherein no non-conductive structure lies directly vertically between the cell region of the top surface of the substrate and the bottom surface of the substrate.

* * * * *